(12) United States Patent
Jia et al.

(10) Patent No.: US 11,830,193 B2
(45) Date of Patent: Nov. 28, 2023

(54) RECOGNITION METHOD OF INTRACRANIAL VASCULAR LESIONS BASED ON TRANSFER LEARNING

(71) Applicant: XI'AN CREATION KEJI CO., LTD., Xi'an (CN)

(72) Inventors: Yannan Jia, Xi'an (CN); Wenjie Wang, Xi'an (CN)

(73) Assignee: XI'AN CREATION KEJI CO., LTD., Xi'an (CN)

( * ) Notice: Subject to any disclaimer, the term of this patent is extended or adjusted under 35 U.S.C. 154(b) by 165 days.

(21) Appl. No.: 17/564,494

(22) Filed: Dec. 29, 2021

(65) Prior Publication Data
US 2022/0164957 A1    May 26, 2022

Related U.S. Application Data

(63) Continuation of application No. PCT/CN2021/128979, filed on Nov. 5, 2021.

(30) Foreign Application Priority Data

Nov. 23, 2020   (CN) .......................... 202011322238.8

(51) Int. Cl.
*G06T 7/00*      (2017.01)
*G06T 7/33*      (2017.01)
(Continued)

(52) U.S. Cl.
CPC ............ *G06T 7/0014* (2013.01); *A61B 6/501* (2013.01); *A61B 6/504* (2013.01); *A61B 6/5235* (2013.01);
(Continued)

(58) Field of Classification Search
CPC ....... G06T 7/0014; G06T 7/337; G06T 7/136; G06T 7/11; G06T 3/40; G06T 5/007;
(Continued)

(56) References Cited

U.S. PATENT DOCUMENTS

| | | | | |
|---|---|---|---|---|
| 2004/0086175 A1* | 5/2004 | Parker | ................... | G06T 11/008 382/128 |
| 2015/0339847 A1* | 11/2015 | Benishti | ................. | A61B 5/026 382/131 |

\* cited by examiner

*Primary Examiner* — Michelle Chin
(74) *Attorney, Agent, or Firm* — WPAT, PC

(57) ABSTRACT

A recognition method of intracranial vascular lesions based on transfer learning is provided, which includes: obtaining a bright-blood image group, a black-blood image group and an enhanced black-blood image group; registering bright-blood images to obtain a registered bright-blood image group; eliminating flowing void artifact to obtain an artifact-elimination enhanced black-blood image group; subtracting each image of the artifact-elimination enhanced black-blood image group from corresponding black-blood image to obtain angiography enhanced images; establishing a blood 3D model; establishing a vascular 3D model with blood boundary expansion; establishing an angiography enhanced 3D model by using the angiography enhanced images; obtaining an intracranial vascular enhanced 3D model based on the blood 3D model, the vascular 3D model and the angiography enhanced 3D model; and obtaining an intracranial vascular lesion recognition model based on the intracranial vascular enhanced 3D model. The method can simply, quickly and intuitively recognize the intracranial vascular lesions clinically.

10 Claims, 7 Drawing Sheets

(51) Int. Cl.
  *G06T 7/136* (2017.01)
  *G06T 7/11* (2017.01)
  *G06T 5/50* (2006.01)
  *G06T 5/00* (2006.01)
  *G06T 3/40* (2006.01)
  *G06T 17/00* (2006.01)
  *G16H 30/20* (2018.01)
  *G16H 50/20* (2018.01)
  *A61B 6/00* (2006.01)

(52) U.S. Cl.
  CPC ............... *G06T 3/40* (2013.01); *G06T 5/007* (2013.01); *G06T 5/50* (2013.01); *G06T 7/11* (2017.01); *G06T 7/136* (2017.01); *G06T 7/337* (2017.01); *G06T 17/00* (2013.01); *G16H 30/20* (2018.01); *G16H 50/20* (2018.01); G06T 2207/20016 (2013.01); G06T 2207/20081 (2013.01); G06T 2207/20084 (2013.01); G06T 2207/20221 (2013.01); G06T 2207/20224 (2013.01); G06T 2207/30096 (2013.01); G06T 2207/30101 (2013.01); G06T 2210/41 (2013.01)

(58) Field of Classification Search
  CPC . G06T 5/50; G06T 17/00; G06T 2207/20016; G06T 2207/20081; G06T 2207/20084; G06T 2207/20221; G06T 2207/20224; G06T 2207/30096; G06T 2207/30101; G06T 2210/41; G16H 30/20; G16H 50/20; A61B 6/501; A61B 6/504; A61B 6/5235
  See application file for complete search history.

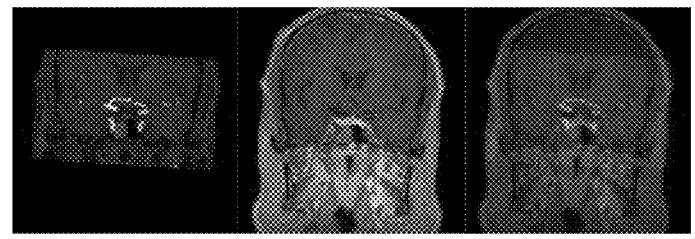
FIG. 7
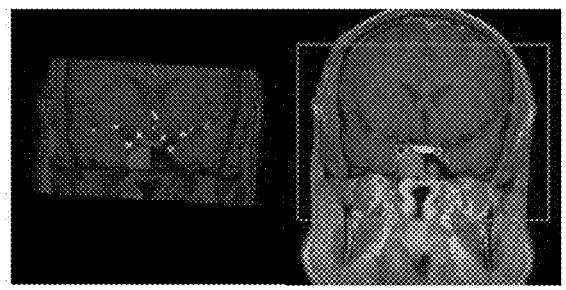
FIG. 8
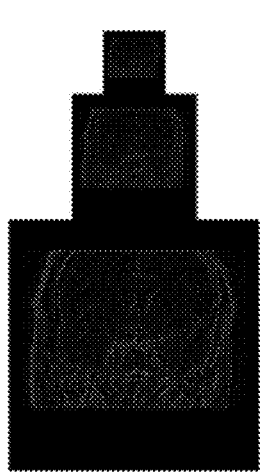 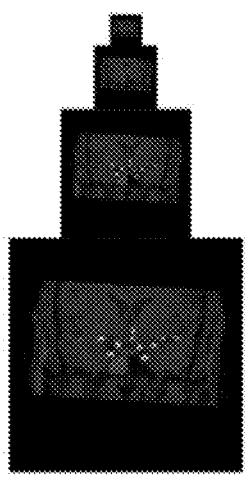 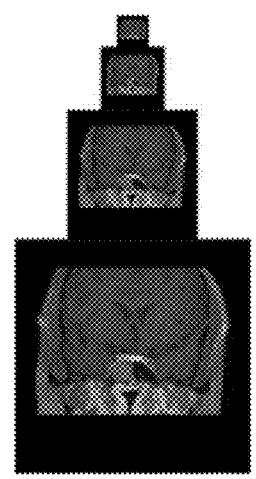 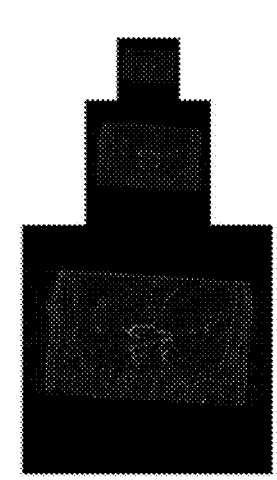
FIG. 9A        FIG. 9B        FIG. 9C        FIG. 9D

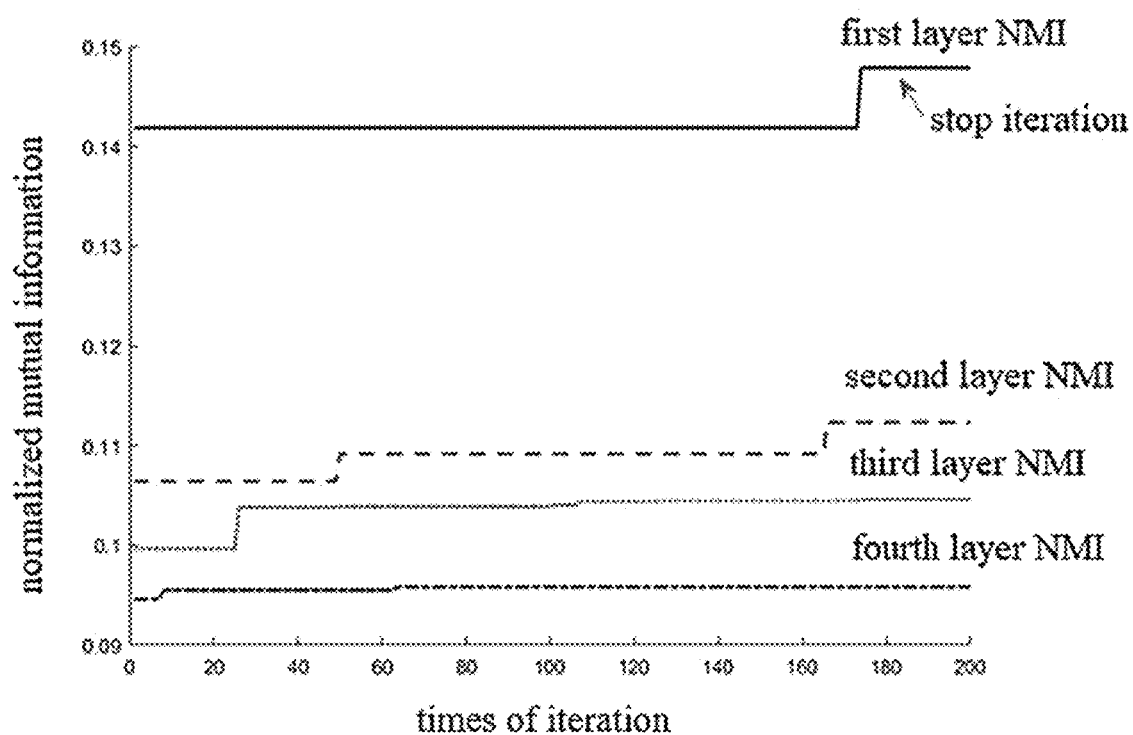
FIG. 12
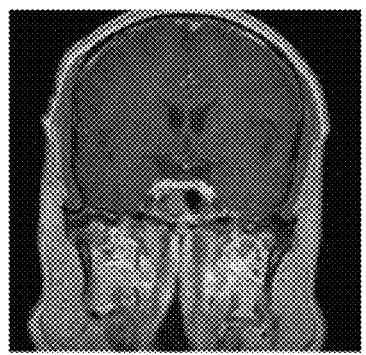 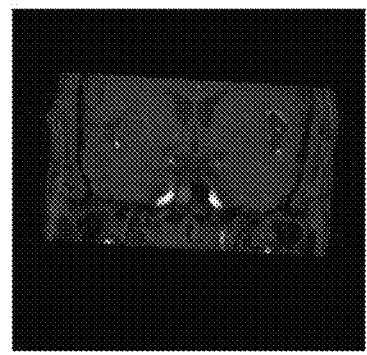 
FIG. 13A    FIG. 13B    FIG. 13C

RECOGNITION METHOD OF INTRACRANIAL VASCULAR LESIONS BASED ON TRANSFER LEARNING

TECHNICAL FIELD

The disclosure relates to the field of image processing, and more particularly to a recognition method of intracranial vascular lesions based on transfer learning.

BACKGROUND

According to the latest medical data, vascular diseases have seriously affected life and health of contemporary people and become one of the diseases with high mortality. For example, atherosclerosis, inflammation-induced vascular diseases, vascular true tumor diseases and so on. The common causes of the vascular diseases are vascular stenosis, vascular plug, vascular rupture, plaque and so on. At present, methods based on vascular cavity imaging are usually used to evaluate degrees of intracranial vascular lesions and vascular stenosis, such as a digital subtraction angiography (DSA), a computed tomography angiography (CTA), a magnetic resonance angiography (MRA) and a high-resolution magnetic resonance angiography (HRMRA).

Among them, the magnetic resonance angiography technology (for example MRA or HRMRA), as a noninvasive imaging method for patients, can clearly detect and analyze the vascular wall structure of the intracranial blood vessels. A scanned magnetic resonance image has a high resolution for a soft tissue, no bone artifacts, good image quality, and can use a variety of sequences scanning to obtain tissue structures with different imaging characteristics, it has obvious advantages in the display of the intracranial blood vessels.

Because of the images corresponding to bright-blood sequences and black-blood sequences obtained by the magnetic resonance angiography are two-dimensional (2D) images, in clinical practice, doctors need to combine the information of the two kinds of images with experience to obtain the comprehensive situation of the intracranial blood vessels for analyzing intracranial vascular diseases. However, the two-dimensional images have limitations, which is not conducive to obtain the real information of intracranial blood vessels simply and quickly

SUMMARY

In order to obtain the real information of blood vessels simply and quickly in clinical application for analyzing vascular diseases. The embodiment of the disclosure provides a recognition method of intracranial vascular lesions based on transfer learning, which may include:

obtaining a bright-blood image group, a black-blood image group and an enhanced black-blood image group of an intracranial vascular site; where the bright-blood image group, the black-blood image group and the enhanced black-blood image group respectively comprise K number of bright-blood images, K number of black-blood images and K number of enhanced black-blood images, the K number of bright-blood images of the bright-blood image group, the K number of black-blood images of the black-blood image group and the K number of enhanced black-blood images of the enhanced black-blood image group are corresponded one by one, and K is a natural number greater than 2;

performing an image registration to each of the K number of bright-blood images by using a corresponding one of the K number of enhanced black-blood images of the enhanced black-blood image group as a reference through a registration method based on mutual information and image pyramid, to obtain a registered bright-blood image group comprising K number of registered bright-blood images;

performing an elimination operation of flowing void artifact to the K number of enhanced black-blood images of the enhanced black-blood image group by using the registered bright-blood image group, to obtain an artifact-elimination enhanced black-blood image group comprising K number of object enhanced black-blood images;

performing a subtraction operation between each of the K number of object enhanced black-blood images of the artifact-elimination enhanced black-blood image group and a corresponding one of the K number of black-blood images of the black-blood image group, to obtain K number of angiography enhanced images;

establishing a blood three-dimensional (3D) model by using the registered bright-blood image group, based on transfer learning;

establishing a vascular 3D model with blood boundary expansion by using the registered bright-blood image group;

establishing an angiography enhanced 3D model by using the K number of angiography enhanced images;

obtaining an intracranial vascular enhanced 3D model based on the blood 3D model, the vascular 3D model and the angiography enhanced 3D model; and obtaining values of target parameters representing degrees of vascular stenosis of respective vascular segments of the intracranial vascular enhanced 3D model, and marking/labeling the intracranial vascular enhanced 3D model by using the values of the target parameters of respective vascular segments, to obtain an intracranial vascular lesion recognition model.

In the solution provided by the embodiment of the disclosure, firstly, the bright-blood image and the enhanced black-blood image scanned by magnetic resonance angiography technology are registered by using the registration method based on mutual information and image pyramid, which can improve the registration efficiency and improve the registration accuracy layer by layer from low resolution to high resolution. Through the above image registration, the bright-blood image and the enhanced black-blood image can be unified in the same coordinate system. Secondly, using the registered bright-blood image to eliminate the flowing void artifact of the enhanced black-blood image can display more accurate and comprehensive vascular information. The solution provided by the embodiment of the disclosure is to eliminate the flowing void artifact from the perspective of image post-processing without using new imaging technology, imaging mode or pulse sequence. Therefore, the flowing void artifact can be eliminated simply, accurately and quickly, and can be well popularized in clinical application. Thirdly, the blood 3D model is established by using the registered bright-blood image, the vascular 3D model with blood boundary expansion is established by using the registered bright-blood image, and the angiography enhanced 3D model is obtained by subtracting the artifact-elimination enhanced black-blood image and black-blood image. Based on the blood 3D model, the vascular 3D model and the angiography enhanced 3D model, the angiography enhanced 3D model corresponding to the vascular wall with angiographic enhancement effect is obtained. Finally, the values of the target parameters representing the degrees of vascular stenosis in the intracranial angiography enhanced 3D model are marked to obtain the intracranial vascular lesion recognition model. The intracranial vascular lesion recognition model realizes the three-dimensional visualization of intracranial blood vessels. It does not need doctors to restore the tissue structure and disease characteristics of intracranial blood vessels through imagination. It can provide vivid three-dimensional spatial information of intracranial blood vessels, facilitate intuitive observation, and locate and display the narrow lesion area. In clinical application, it can simply, quickly and intuitively obtain the real information of intracranial blood vessels and the analysis data of the degree of intracranial vascular stenosis.

BRIEF DESCRIPTION OF DRAWINGS

FIG. 7 shows a result of intracranial vascular magnetic resonance images after pre-registration according to an embodiment of the disclosure.

FIG. 8 shows an area to be registered of the intracranial vascular magnetic resonance images according to the embodiment of the disclosure.

FIGS. 9A-9B are schematic diagrams of a bright-blood Gaussian pyramid and a black-blood Gaussian pyramid of the intracranial vascular magnetic resonance images respectively according to the embodiment of the disclosure.

FIGS. 9C-9D are schematic diagrams of a bright-blood Laplacian pyramid and a black-blood Laplacian pyramid of the intracranial vascular magnetic resonance images respectively according to the embodiment of the disclosure.

FIG. 12 a schematic diagram of normalized mutual information under different iteration times according to an embodiment of the disclosure.

FIGS. 13A-13E show registration results of the intracranial vascular magnetic resonance images of multiple registration methods according to the embodiment of the disclosure.

DETAILED DESCRIPTION OF EMBODIMENTS

In order to obtain the real information of blood vessels simply and quickly in clinical application for the analysis of vascular diseases. The embodiment of the disclosure provides a recognition method of intracranial vascular lesions based on transfer learning.

Figure 1:
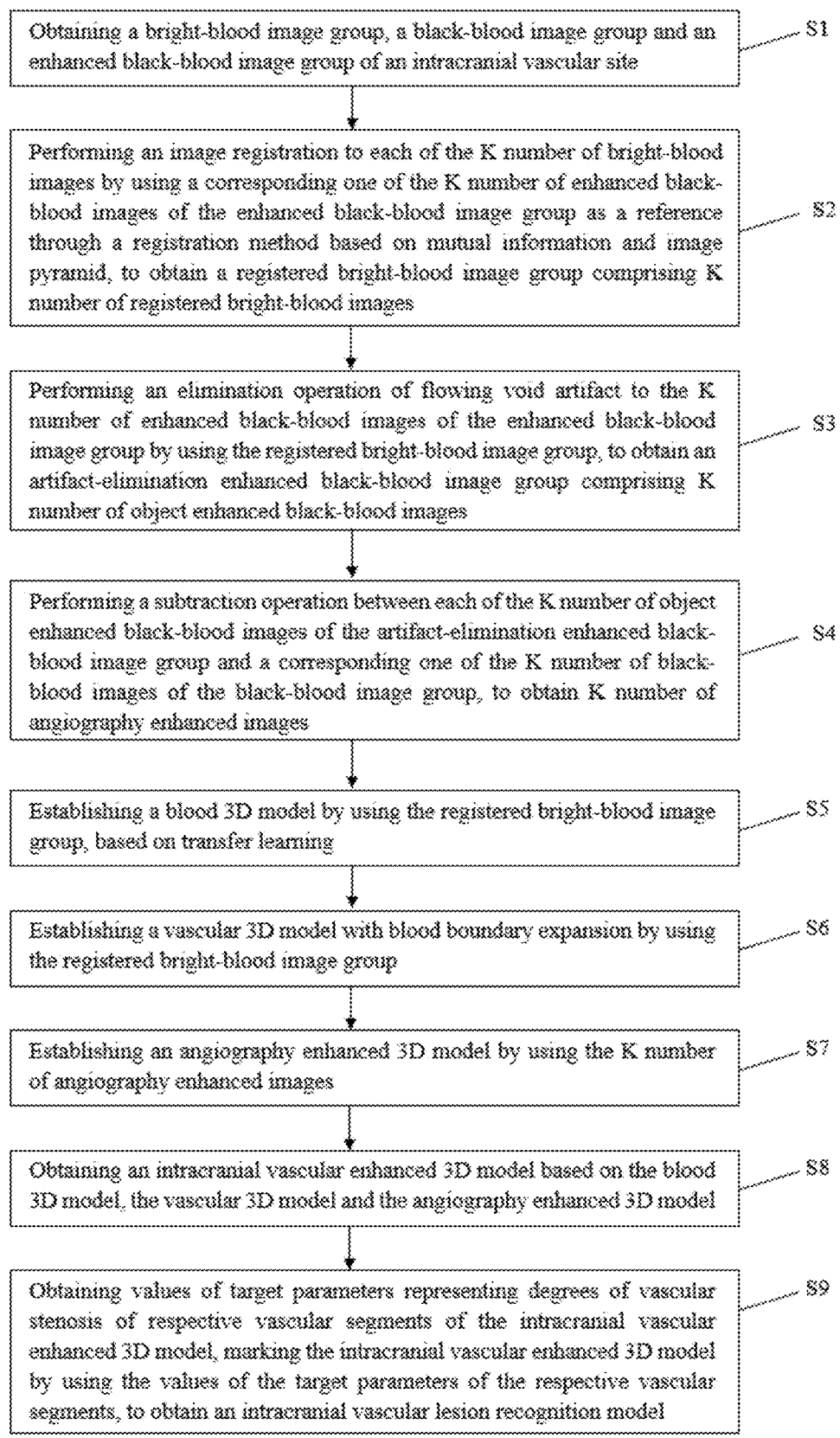
FIG. 1 is a flowchart of a recognition method of intracranial vascular lesions based on transfer learning according to an embodiment of the disclosure.

As shown in FIG. 1, FIG. 1 is a flowchart of a recognition method of intracranial vascular lesions based on transfer learning provided by an embodiment of the disclosure, which may be executed by a computer system including one or more memories and one or more processors coupled to the one or more memories. The recognition method may include step 1 (also referred to as S1) through step 9 (also referred to as S9) as follows.

S1, obtaining a bright-blood image group, a black-blood image group and an enhanced black-blood image group of an intracranial vascular site.

Specifically, the bright-blood image group, the black-blood image group and the enhanced black-blood image group respectively include K number of bright-blood images, K number of black-blood images and K number of enhanced black-blood images. The K number of bright-blood images of the bright-blood image group, the K number of black-blood images of the black-blood image group and the K number of enhanced black-blood images of the enhanced black-blood image group are corresponded one by one, and K is a natural number greater than 2.

In the illustrated embodiment of the disclosure, the magnetic resonance angiography technology is, for example, HRMRA.

The K number of bright-blood images of the bright-blood image group, the K number of black-blood images of the black-blood image group and the K number of enhanced black-blood images of the enhanced black-blood image group are corresponded one by one; and the corresponding mode is that the order images formed according to the scanning time is the same.

S2, performing an image registration to each of the K number of bright-blood images by using a corresponding one of the K number of enhanced black-blood images of the enhanced black-blood image group as a reference through a registration method based on mutual information and image pyramid, to obtain a registered bright-blood image group including K number of registered bright-blood images.

Specifically, the S2 is actually to complete the image registration of each of the K number of bright-blood images, that is, each of the K number of bright-blood images to be registered is taken as a floating image, the enhanced black-blood image corresponding to the bright-blood image is taken as a reference image, a similarity measure based on mutual information is used, and image pyramid is introduced for the image registration.

In an illustrated embodiment, S2 may include step 21 (also referred to as S21) through step 27 (also referred to as S27):

S21, preprocessing each of the K number of bright-blood images and the corresponding one of the K number of enhanced black-blood images to obtain a first bright-blood image and a first black-blood image.

Alternatively, the S21 may include step 211 (also referred to as S211) and step 212 (also referred to as S212):

S211, for each of the K number of bright-blood images, taking the corresponding enhanced black-blood images as a reference, performing a coordinate transformation and an image interpolation to the bright-blood image by using a similarity measure based on mutual information and adopting a predetermined search strategy to thereby obtain a pre-registered first bright-blood image;

The S211 is actually an image pre-registration of the bright-blood image based on the enhanced black-blood image.

Specifically, the enhanced black-blood images and the bright-blood images are the images to be registered. According to the orientation label information in the digital imaging and communications in medicine (DICOM) file of the bright-blood images, the enhanced black-blood images can be used as the reference images, the bright-blood images can be used as the floating images, and each of the bright-blood images can be performed the coordinate transformation to realize the purpose of rotating the bright-blood image to a same coordinate system as the corresponding one enhanced black-blood image. After rotation, the scanning direction of the bright blood image also changes to be a coronal plane.

Through the pre-registration of the S211, the magnetic resonance images at the same scanning level can be initially compared in the same coordinate system. However, due to the different scanning times of bright-blood sequence and black-blood sequence, and the patient may have slight movement before and after scanning, the above operation is only a rough coordinate transformation, only the pre-registration cannot realize the complete registration of multimodal magnetic resonance images, but this step can omit unnecessary processing process for the subsequent accurate registration link and improve the processing speed.

S212, extracting content of an area same as a scanning range of the first bright-blood image from the corresponding enhanced black-blood image to form the first black-blood image.

Alternatively, S212 may include the following steps:

1. obtaining vascular edge contour information in the first bright-blood image.

Specifically, Sobel edge detection method can be used to obtain the edge contour information. The edge contour information includes the coordinate values of each edge point.

2. extracting minimum and maximum of abscissa and minimum and maximum of ordinate in the edge contour information to obtain four coordinate values, and determining an initial extraction boundary based on the four coordinate values.

That is, in the edge contour information, extracting the minimum of the abscissa, the maximum of the abscissa, the minimum of the ordinate and the maximum of the ordinate, and using these four coordinate values to determine the four vertexes of the square boundary, so as to obtain the initial extraction boundary.

3. expanding the initial extraction boundary by a preset number of pixels in each of four directions within a size range of the first bright-blood image, to obtain a final extraction boundary (also referred to as the scanning range of the first bright-blood image);

The four directions are positive direction of the abscissa, negative direction of the abscissa, positive direction of ordinate and negative direction of ordinate. The preset number is reasonably selected according to the type of the vascular image to ensure that the expanded final extraction boundary does not exceed the size range of the first bright-blood image. For example, the preset number can be 20.

4. extracting content of an area corresponding to the final extraction boundary in the enhanced black-blood image, to form the first black-blood image.

According to the coordinate range delimited by the final extraction boundary, the content of the corresponding area in the enhanced black-blood image is extracted, and the extracted content is formed into the first black-blood image. This step extracts the area to be registered to obtain the common scanning range of magnetic resonance images in two modes, which is conducive to the subsequent rapid registration.

In the illustrated embodiment of the disclosure, in order to improve the accuracy of the image registration and avoid the image converging to the local maximum in the registration process, the multi-resolution strategy is selected to solve the problem of local extreme value. At the same time, the multi-resolution strategy is used to improve the execution speed of the algorithm and increase the robustness under the condition of meeting the image registration accuracy. Therefore, the image pyramid method is adopted. Optionally, the following steps can be taken:

S22, obtaining a bright-blood Gaussian pyramid according to the first bright-blood image and a black-blood Gaussian pyramid according to the first black-blood image based on down-sampling processing; where each of the bright-blood Gaussian pyramid and the black-blood Gaussian pyramid includes m number of images with resolution decreased gradually from bottom to top, and m is a natural number greater than 3;

In an illustrated embodiment, S22 may include the following steps:

obtaining an input image of i-th layer, filtering the input image of the i-th layer with Gaussian kernel, deleting even rows and even columns of the filtered image to obtain an image $G_i$ of the i-th layer of the Gaussian pyramid, and taking the image $G_i$ of the i-th layer as an input image of (i+1)-th layer to obtain an image $G_{i+1}$ of the (i+1)-th layer of the Gaussian pyramid, where i=1,2, . . . , m−1; when the Gaussian pyramid is the bright-blood Gaussian pyramid, the input image of the first layer is the first bright-blood image; when the Gaussian pyramid is the black-blood Gaussian pyramid, the input image of the first layer is the first black-blood image.

Specifically, multiple images in the Gaussian pyramid are images corresponding to the same original image with different resolutions. Gaussian pyramid obtains the image through Gaussian filtering and down-sampling, construction steps of each layer of the Gaussian pyramid can be divided into two steps: firstly, using Gaussian filtering to smooth the image, that is, Gaussian kernel is used to filter; then, the even rows and the even columns of the filtered image are deleted, that is, the width and height of the image of the lower layer are reduced by half to obtain the image of the current layer. Therefore, the image of the current layer is one fourth of the size of the image of the lower layer. Through continuous iteration of the above steps, the Gaussian pyramid can be obtained.

In this step, through the above processing of the first bright-blood image and the first black-blood image after the preprocessing, the bright-blood Gaussian pyramid and the black-blood Gaussian pyramid can be obtained. The number of image layers m may be 4.

Because the Gaussian pyramid is down-sampling, that is, reducing the image, part of the image data will be lost. Therefore, in the embodiment of the disclosure, in order to avoid the data loss of the image in the scaling process and recover the detail data, the Laplace pyramid is used in the subsequent steps to realize image reconstruction together with the Gaussian pyramid, and highlight the details on the basis of the Gaussian pyramid image.

S23, obtaining a bright-blood Laplace pyramid according to the bright-blood Gaussian pyramid and a black-blood Laplace pyramid according to the black-blood Gaussian pyramid based on up-sampling processing; where each of the bright-blood Laplacian pyramid and the black-blood Laplacian pyramid includes m−1 number of images with resolution decreased gradually from bottom to top.

In an illustrated embodiment, S23 may include the following steps:
performing the up-sampling to the image $G_{i+1}$ of the (i+1)-th layer of the Gaussian pyramid, and filling new-added rows and columns with data 0 to obtain a filled image;
performing convolution to the filled image by using the Gaussian kernel to obtain an approximate value of the filled pixels and obtaining an enlarged image;
performing subtraction operation between the image $G_{i+1}$ of the (i+1)-th layer of the Gaussian pyramid and the enlarged image to obtain an image $L_i$ of the i-th layer of the Laplacian pyramid;

Among them, when the Gaussian pyramid is the bright-blood Gaussian pyramid, the Laplacian pyramid is the bright-blood Laplacian pyramid; and when the Gaussian pyramid is the black-blood Gaussian pyramid, the Laplacian pyramid is the black-blood Laplacian pyramid.

Because of the Laplacian pyramid is the residual error between the original image and the original image after the down-sampling, compared along the direction from bottom to top, the Laplacian pyramid has one layer less high-layer image than the Gaussian pyramid structure.

Specifically, the mathematical formula for generating the Laplacian pyramid structure is shown in (1), which $L_i$ represents the i-th layer of the Laplacian pyramid (such as the bright-blood Laplacian pyramid or the black-blood Laplacian pyramid), $G_i$ represents the i-th layer of the Gaussian pyramid (such as the bright-blood Gaussian pyramid or the black-blood Gaussian pyramid), UP represents up-sampling for image enlarging, $\otimes$ is a convolution symbol, and $\varsigma_{5\times5}$ is the Gaussian kernel used in building the Gaussian pyramid. This formula shows that the Laplace pyramid is essentially composed of subtracting the data of the residual error of the image of first reduced and then enlarged from the original image. The Laplace pyramid is a residual error prediction pyramid. The core idea of the Laplace pyramid is to store the difference between the original image and the original image after the down-sampling operation and retain the high-frequency information of the image, the purpose is to completely restore the image before the down-sampling at each layer. Because of a part of the information lost in the previous down-sampling operation cannot be completely recovered by the up-sampling, that is, the down-sampling is irreversible, the display effect of the image after down-sampling and then up-sampling is blurred than the original image. By storing the residual error between the original image and the original image after the down-sampling operation, the details can be added to the images of different frequency layers and highlighted on the basis of Gaussian pyramid image.

$$L_i = G_i - \mathrm{UP}(G_{i+1}) \otimes \varsigma_{5\times5} \qquad (1)$$

Corresponding to the 4 layers Gaussian pyramid, this step can obtain the bright-blood Laplacian pyramid and the black-blood Laplacian pyramid with 3 layers of image.

S24, registering the images in each layer of the bright-blood Laplacian pyramid with the image in a corresponding layer of the black-blood Laplacian pyramid to obtain a registered bright-blood Laplacian pyramid.

In an illustrated embodiment, the S24 may include the following steps:
for each layer of the bright-blood Laplacian pyramid and the black-blood Laplacian pyramid, using the black-blood Laplacian image corresponding to this layer as the reference image, using the bright-blood Laplacian image corresponding to this layer as the floating image, using the similarity measure based on mutual information and adopting the predetermined search strategy to realize the image registration, and thereby obtaining the registered bright-blood Laplace image of this layer;
obtaining the registered bright-blood Laplacian pyramid composed of multi-layer registered bright-blood Laplacian images arranged along the direction from bottom to top according to the order of decreasing resolution. Among them, the black-blood Laplacian image is one of the images of the black-blood Laplacian pyramid, and the bright-blood Laplacian image is one of the images of the bright-blood Laplacian pyramid.

The registration process in this step is similar to the previous pre-registration process. By performing the coordinate transformation and the image interpolation to the bright-blood Laplacian image, using the similarity measurement and the predetermined search strategy to realize the image registration, and the registered bright-blood Laplacian image can be obtained.

S25, registering the images in respective layers of the bright-blood Gaussian pyramid with the images in corresponding layers of the black-blood Gaussian pyramid respectively from top to bottom by using the registered bright-blood Laplace pyramid as superposition information to obtain a registered bright-blood Gaussian pyramid.

For the S25, the registered bright-blood Laplacian pyramid is used as the superposition information to register the images in respective layers of the bright-blood Gaussian pyramid and the black-blood Gaussian pyramid from top to bottom, images with different resolutions in the Gaussian pyramid need to be registered. Since the registration of low-resolution images can more easily grasp the essential characteristics of the image, the embodiment of the disclosure registers high-resolution images on the basis of low-resolution image registration, that is, the Gaussian pyramid image is registered along the direction from top to bottom, the registration result of the image of the upper layer (also referred to as the previous layer) is used as the input of the image registration of the lower layer (also referred to as the current layer).

In an illustrated embodiment, the S25 may include the following steps:
for an j-th layer from top to down of each of the bright-blood Gaussian pyramid and the black-blood Gaussian pyramid, using a black-blood Gaussian image corresponding to the j-th layer of the black-blood Gaussian pyramid as a reference image and a bright-blood Gaussian image corresponding to the j-th layer of the bright-blood Gaussian pyramid as a floating image, using a similarity measure based on mutual information and adopting a predetermined search strategy to realize the registering of images, thereby obtaining a registered bright-blood Gaussian image of the j-th layer;

performing an up-sampling operation to the registered bright-blood Gaussian image of the j-th layer, adding the registered bright-blood Gaussian image of the j-th layer after the up-sampling operation with a registered bright-blood Laplacian image of a corresponding layer of the registered bright-blood Laplacian pyramid to obtain an added image, and replacing a bright-blood Gaussian image of a (j+1)th layer of the bright-blood Gaussian pyramid by the added image; and taking a black-blood Gaussian image of the (j+1)th layer of the black-blood Gaussian pyramid as a reference image and the bright-blood Gaussian image of the (j+1)th layer after the replacing as a floating image, using a predetermined similarity measure and a predetermined search strategy to realize the registering and thereby obtain a registered bright-blood Gaussian image of the (j+1)th layer; and j=1, 2, ..., m−1; each the black-blood Gaussian image is one of the m number of images of the black-blood Gaussian pyramid, and each the bright-blood Gaussian image is one of the m number of images of the bright-blood Gaussian pyramid.

Repeat the above steps until the high-resolution registration of the Gaussian pyramid image of bottom layer is completed to obtain the registered bright-blood Gaussian pyramid. The coordinate system of the bright-blood image is consistent with that of the black-blood image, and the image has high similarity. The registration process is similar to the above previous pre-registration process and will not be repeated.

S26, obtaining K number of registered bright-blood images corresponding to the K number of bright-blood images respectively based on the registered bright-blood Gaussian pyramid.

In this step, the bottom images in the registered bright-blood Gaussian pyramid are obtained as the registered bright-blood images.

S27, obtaining the registered bright-blood image group according to the K number of bright-blood images corresponding to the K number of registered bright-blood images.

After all the bright-blood images are registered, the registered bright-blood image group can be obtained from the K number of registered bright-blood images. Each registered bright-blood image and the corresponding enhanced black-blood image can be used as a registered image pair.

Through the above steps, the image registration of the bright-blood image and the enhanced black-blood image can be realized. In the registration solution provided by the embodiment of the disclosure, the registration accuracy can be improved based on mutual information as the similarity measure. Moreover, the pyramid algorithm is used to register the magnetic resonance bright-blood image and black-blood image of vascular site, which can improve the registration efficiency and improve the registration accuracy layer by layer from low resolution to high resolution. Through the above image registration, the bright-blood image and the enhanced black-blood image can be unified in the same coordinate system, which can facilitate doctors to understand the vascular images corresponding to black-blood sequence and bright-blood sequence, obtain the comprehensive information required for diagnosis simply and quickly, and provide accurate and reliable reference information for subsequent medical diagnosis, making operation plan and radiotherapy plan. The registration solution provided by the embodiment of the disclosure can provide a better reference mode for other medical image registration, and has great clinical application value. Furthermore, the image registration process of the embodiment of the disclosure is an important basis for the subsequent elimination of flowing void artifact.

After the image registration, the flowing void artifact in the registered enhanced black-blood image can be eliminated. The reason for the flowing void artifact is that in the process of vascular wall imaging, due to the blood vessels is too thin, the flow velocity at the detour of blood is slow, and the surrounding blood and tissue fluid can have signal pollution problem. In the images obtained by black-blood sequence scanning, the blood information that should be black appears as bright color instead, so as to simulate the wall thickening or plaque appearance of normal individuals and exaggerate the degree of vascular stenosis. The embodiment of the disclosure considers using the blood information in the registered bright-blood image to correct the blood information with incorrect signal display in the registered enhanced black-blood image, and embedding the blood information in the registered bright-blood image into the registered enhanced black-blood image, so as to achieve the effect of image fusion. It can be achieved through the following steps:

S3, performing an elimination operation of flowing void artifact to the K number of enhanced black-blood images of the enhanced black-blood image group by using the registered bright-blood image group, to obtain an artifact-elimination enhanced black-blood image group comprising K number of object enhanced black-blood images;

In an illustrated embodiment, the S3 may include step 31 (also referred to as S41) through step 34 (also referred to as S34):

S31, improving contrast of each of the K number of registered bright-blood images to obtain a contrast-enhanced bright-blood image, thereby obtaining K number of contrast-enhanced bright-blood images;

For the specific process of gray-scale linear transformation, please refer to the relevant prior art and will not be repeated here.

S32, extracting the blood information from each of the K number of contrast-enhanced bright-blood images to obtain a bright-blood feature image;

In an illustrated embodiment, S32 may include step 321 (also referred to as S321) through step 323 (also referred to as S323):

S321, determining a first threshold by using a preset image binarization method;

S322, extracting the blood information from each of the K number of contrast-enhanced bright-blood images by using the first threshold;

The method used in the step S322 is called threshold segmentation.

S323, obtaining the bright-blood feature image according to the extracted blood information.

The preset image binarization method is the binarization processing of the image. The gray level of the points on the image can be set to 0 or 255, that is, the whole image presents an obvious black-and-white effect. That is, the gray images with 256 brightness levels can obtain a binary image that still reflect the overall and local characteristics of the image through appropriate threshold selection. Through the preset image binarization method, the embodiment of the disclosure can highlight the blood information in the contrast-enhanced bright-blood image as white and display the irrelevant information as black, so as to extract the bright-blood feature image corresponding to the blood information.

The preset image binarization method in the embodiment of the disclosure can include the maximum interclass variance method (OTSU), kittle, etc.

The extraction formula of the blood information is shown in (2), where T (x, y) represents the gray value of the contrast-enhanced bright-blood image, F (x, y) represents the gray value of the bright-blood feature image, and T represents the first threshold;

$$F(x, y) = \begin{cases} 1 & T(x, y) \geq T \\ 0 & T(x, y) < T \end{cases}. \quad (2)$$

S33, fusing each of the K number of bright-blood feature images with the enhanced black-blood image corresponding to the registered bright-blood image according to a preset image fusion formula to obtain the object enhanced black-blood image of elimination of flowing void artifact corresponding to the enhanced black-blood image;

In this step, firstly, the spatial mapping relationship between the bright-blood feature image and the corresponding enhanced black-blood image is established, the bright-blood feature image is mapped to the corresponding enhanced black-blood image, and the image fusion is carried out according to the preset fusion formula, the preset fusion formula is:

$$g(x, y) = \begin{cases} 0 & F(x, y) > 0 \\ R(x, y) & F(x, y) = 0 \end{cases}; \quad (3)$$

where, F (x, y) represents the gray value of the bright-blood feature image, R(x, y) represents the gray value of the corresponding enhanced black-blood image, and g(x, y) represents the gray value of the object enhanced black-blood image after the fusion.

Through the above operations, the gray value of the flowing void artifact in the corresponding enhanced black-blood image, which should be black but appears as bright color, can be changed to black, so as to achieve the purpose of eliminating the flowing void artifact.

S34, obtaining the artifact-elimination enhanced black-blood image group according to the object enhanced black-blood images respectively corresponding to the K number of enhanced black-blood images.

After all the enhanced black-blood images have completed the elimination of flowing void artifact, the artifact-elimination enhanced black-blood image group can be obtained.

S4, performing a subtraction operation between each of the K number of object enhanced black-blood images of the artifact-elimination enhanced black-blood image group and a corresponding one of the K number of black-blood images of the black-blood image group, to obtain K number of angiography enhanced images.

Each object enhanced black-blood image is subtracted from the corresponding black-blood image to obtain the angiography enhanced image with angiography enhancement effect. When all object enhanced black-blood images are subtracted from the corresponding black-blood images, the K number of angiography enhanced images can be obtained. It can be understood that the K number of angiography enhanced images are two-dimensional images.

S5, establishing a blood 3D model by using the registered bright-blood image group, based on transfer learning.

In an illustrated embodiment, the S5 may include step 51 (also referred to as S51) through step 54 (also referred to as S54):

S51, projecting the registered bright-blood image group in three preset directions by using a maximum intensity projection (MIP) method to obtain maximum intensity projection images respectively in the three preset directions.

The maximum intensity projection method is one of the computed tomography (CT) three-dimensional image reconstruction technology, which is called MIP. Specifically, when the optical fiber bundle passes through the original image of a section of tissue, the pixels with the highest density in the image are retained and projected onto a 2D plane to form the MIP reconstructed image (also referred to as MIP image for short in the embodiment of the disclosure). MIP can reflect the X-ray attenuation value of corresponding pixels, and small density changes can also be displayed on MIP images. It can well display the vascular stenosis, vasodilatation, vascular filling defect, and distinguish the calcification on the vascular wall from the contrast agent in the vascular cavity.

Figure 2:
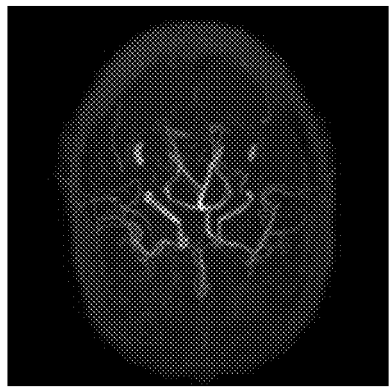
FIG. 2 is a maximum intensity projection (MIP) image as an example of according to an embodiment of the disclosure.

It can be understood by those skilled in the art that after the registration, the bright-blood image group is actually a 3D volume data. The 3D volume data can be projected in the preset three directions by using the above MIP method to obtain a 2D MIP image in each direction, and the preset three directions include axial, coronal and sagittal directions. For the MIP method, please refer to the relevant introduction of the prior art, which will not be repeated here. Referring to FIG. 2, which is a MIP diagram as an example of the embodiment of the disclosure.

S52, taking the MIP images as a target domain and fundus vascular images as a source domain, obtaining 2D vascular segmentation images respectively corresponding to the MIP images in the three preset direction based on the transfer learning.

It is found that the MIP images of bright-blood sequence of intracranial blood vessels has the distribution of vascular tree similar to that of fundus blood vessels. Therefore, the transfer learning method is considered to use, specifically the way of feature transfer is adopted, so that a pre-trained model of fundus vascular (source domain) segmentation task is transferred to an intracranial vascular segmentation task. The feature transfer (Feature based TL) assumes that the source domain and the target domain contain some common cross features, transforms the features of the source domain and the target domain into the same space through feature transformation, so that the source domain data and the target domain data have the same data distribution in this space, and then carries out traditional machine learning.

For the S52, in an illustrated embodiment, may include step 521 (also referred to as S521) to step 523 (also referred to as S523):

S521, obtaining a pre-trained target neural network for a segmentation task of the fundus vascular images;

among them, the target neural network is obtained by pre-training according to a dataset of the fundus vascular images and an improved U-net network model.

As mentioned above, the embodiment of the disclosure transfers the pre-trained model of fundus vascular (source domain) segmentation task to the intracranial vascular segmentation task with the help of the transfer learning of the feature transfer. Therefore, it is necessary to obtain a mature network model for vascular segmentation of fundus vascular images. Specifically, the obtaining the per-trained target neural network can be divided into step A through step B:

step A: obtaining an original network model;

in the embodiment of the disclosure, the structure of the existing U-net network model can be improved, and each sub-module can be replaced with a residual module with residual connection form to obtain the improved U-net network model. In the embodiment of the disclosure, the residual module is introduced into the U-net network model, which can effectively solve the problem that the gradient disappears due to the deepening of the layers of the neural network, so that the training error does not decrease but increases.

step B: obtaining a sample data of the fundus vascular images; and the embodiment of the disclosure obtains the dataset of the fundus vascular images, that is, DRIVE dataset, which is a marked dataset.

step C, training the original network model by using the sample data of the fundus vascular image to obtain the pre-trained target neural network.

Some parameter characteristics of the target neural network according to the embodiment of the disclosure are briefly introduced below.

The improved U-net network model in the embodiment of the disclosure has five levels to form a ladder network with 2.5 M parameters. Each residual module uses a dropout rate of 0.25 (dropout means that neural network units are temporarily discarded from the network according to a certain probability during the training of deep learning network. Generally, dropout rate can be set to be 0.3-0.5); and batch normalization (BN) is used to change the size of variance and position of mean value by optimization, so that the new distribution is more suitable for the real distribution of data, thereby ensuring the nonlinear expression ability of the model. The activation function adopts Leakyrelu. The last layer of the network model is activated by using Softmax.

Moreover, due to the uneven distribution of foreground and background of medical image samples, the loss function uses the Dice coefficient loss function commonly used in medical image segmentation, and specifically uses the improved Dice loss function to solve the unstable situation of Dice loss function training.

In the aspect of neural network optimization, Adam optimization algorithm and default parameters are adopted, and the batch size is 256. 250 epochs are trained by using a "reduced learning rate" strategy. The learning rates on epochs 0, 20 and 150 are set to be 0.01, 0.001 and 0.0001 respectively, and the total learning rate is set to be 250. The random clipping method is used for data enhancement to expand the training samples in the DRIVE dataset by 20000 times.

The above briefly introduces the acquisition process of the target neural network. The trained target neural network can realize the vascular segmentation of the fundus vascular image and obtain the corresponding 2D vascular segmentation image.

S522, performing gray inversion and contrast enhancement to the MIP images in the three preset directions to thereby obtain feature MIP images corresponding to the MIP images;

The realization of feature transfer learning requires a high degree of similarity between the source domain (fundus vascular images) and the target domain (intracranial vascular bright-blood sequence MIP mages) to achieve the same data distribution.

Therefore, in the S522, the MIP images are subjected to the gray inversion and contrast enhancement to obtain the feature MIP images, so that the feature MIP images are closer to the fundus vascular image.

In an illustrated embodiment, the S522 may include step 5221 (also referred to as S5221) and step 5222 (also referred to as S5222):

S5221, performing pixel transformation on the MIP images by using a gray inversion formula to obtain inversion images; and the gray inversion formula is $T(x)=255-x$, where x represents a pixel value in a corresponding one of the MIP image, and $T(x)$ is a pixel value in a corresponding one of the inversion images.

Figure 3:
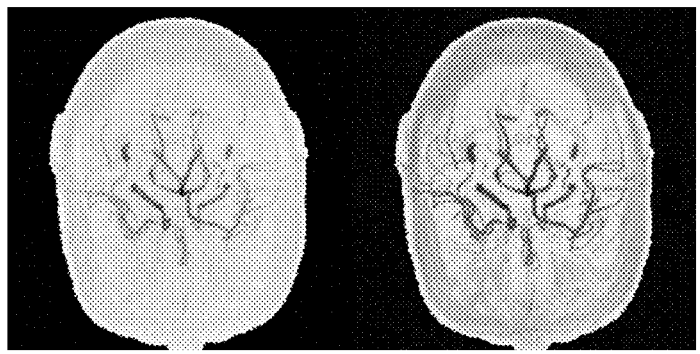
FIG. 3 shows an inversion image corresponding to the MIP image and a feature MIP image corresponding to the MIP image according to the embodiment of the disclosure.

This step can be commonly understood as gray level inversion processing. Since the pixel range of each of the MIP images is between 0 and 255, the original bright area can be darkened and the original dark area can be lightened through this step. Specifically, it can be realized by the pixel transformation through the above gray inversion formula. Referring to FIG. 3, the left image in FIG. 3 is an inversion diagram corresponding to the MIP diagram of the embodiment of the disclosure.

S5222, enhancing a contrast of the inversion images by using a limited contrast adaptive histogram equalization method to obtain the feature MIP images.

The main purpose of this step is to enhance the contrast of the inversion image to show a clearer vascular distribution. Referring to FIG. 3, the right image in FIG. 3 is a feature MIP diagram corresponding to the MIP diagram of the embodiment of the disclosure. It can be seen that the contrast of the feature MIP image is significantly enhanced and the blood vessels are clearer than that of the inversion image.

After the S5222, the corresponding feature MIP image can be obtained for the MIP image in each direction.

In the embodiment of the disclosure, considering that the MIP image of intracranial vascular bright-blood sequence has cross features with the fundus vascular image, the transfer learning method of feature transfer is adopted to map features of the MIP images to the fundus vascular image, so that the intracranial vascular input samples and fundus vascular input samples corresponding to the target neural network have the same sample distribution. Among them, the S521 and the S522 can be in no order.

S523, inputting the feature MIP images in the three preset directions into the target neural network to obtain the 2D vascular segmentation images corresponding to the feature MIP images.

The feature MIP image of each direction is input into the target neural network to obtain the 2D vascular segmentation image corresponding to each direction, the obtained 2D vascular segmentation image is a binary image, that is, the pixels are only 0 and 255, white represents blood vessels and black represents background.

S53, synthesizing the 2D vascular segmentation images in the three preset directions by using a back projection method to obtain a first 3D vascular volume data.

In the back projection method, the pixel values can be controlled. In the embodiment of the disclosure, through the pixel control of the back projection method, voxel values of a vascular part in the first 3D vascular volume data each are 0 and voxel values of a non-vascular part each are negative infinity.

S54, obtaining an intracranial vascular simulation 3D model (also referred to as the blood 3D model) based on the first 3D vascular volume data and a second 3D vascular volume data corresponding to the registered bright-blood image group.

In an illustrated embodiment, the S54 may include step 541 (also referred to as S541) and (also referred to as S542):

S541, adding the first 3D vascular volume data and the second 3D vascular volume data to obtain a third 3D vascular volume data;

The voxel values in the first 3D vascular volume data and the second 3D vascular volume data can be directly added to obtain the third 3D vascular volume data. Through this step, the cerebrospinal fluid and fat signals that have the same intensity as the intracranial vascular signals can be eliminated.

S542, processing the third 3D vascular volume data by using a threshold segmentation method to obtain the intracranial vascular simulation 3D model.

The threshold segmentation method adopted in the embodiment of the disclosure includes the interclass variance method, maximum entropy, iterative method, adaptive threshold, manual, basic global threshold method, etc. In an illustrated embodiment, the embodiment of the disclosure can adopt the maximum interclass variance method.

The maximum interclass variance method (also referred to as OTSU method, or OTSU for short) is a method for automatically obtaining the threshold suitable for bimodal situations. S542 using the OTSU can include the following steps:

firstly, using the OTSU to calculate a first threshold corresponding to a middle fourth 3D vascular volume data in the third 3D vascular volume data.

In this step, the OTSU method is used to calculate a threshold corresponding to a plurality of images in a small cube (called the fourth 3D vascular volume data) near a middle part located in the large 3D cube (the third 3D vascular volume data) is used as the first threshold. Because in the third 3D vascular volume data, the blood information is basically concentrated in the middle of the image, the middle small cube data (the fourth 3D vascular volume data) is selected for determining the first threshold, which can reduce the amount of threshold calculation and improve the calculation speed, and the first threshold can be accurately applicable to all blood information in the third 3D vascular volume data.

For the size of the fourth 3D vascular volume data, the center point of the third 3D vascular volume data can be determined first, and then extend in six directions corresponding to the cube with the preset side length, so as to determine the size of the fourth 3D vascular volume data. Among them, the preset side length can be determined according to the empirical value including Willis ring, such as ¼ of the side length of the cube of the third 3D vascular volume data, and the Willis ring is the most important collateral circulation pathway in the brain, connecting the bilateral hemispheres with the anterior and posterior circulation.

Then, performing the threshold segmentation on the third 3D vascular volume data by using the first to thereby obtain the intracranial vascular simulation 3D model.

Figure 4:
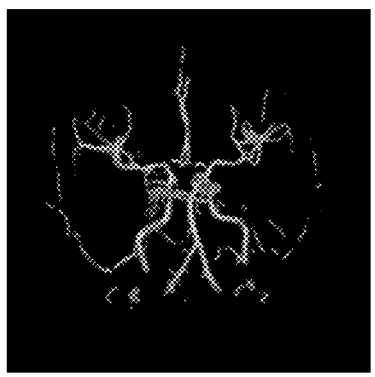
FIG. 4 shows effect of an intracranial vascular simulation three-dimensional (3D) model according to an embodiment of the disclosure.

It can be understood by those skilled in the art that through the threshold segmentation, the gray value of the point on the image corresponding to the third 3D vascular volume data can be set to be 0 or 255, that is, the whole image presents an obvious black-and-white effect, the blood information is highlighted as white, and the irrelevant information is displayed as black. For the processing process of the threshold segmentation, please refer to the prior art and will not be repeated here. The obtained intracranial vascular simulation 3D model is shown FIG. 4, and FIG. 4 shows effect of the intracranial vascular simulation 3D model according to the embodiment of the disclosure. The image is grayed and the color is not shown. In practice, the image can be displayed in color, such as red to display the vascular area.

In the embodiment of the disclosure, the research idea of the transfer learning is applied to the segmentation field of intracranial blood vessels, and a more accurate vascular segmentation effect can be obtained. Moreover, the first 3D vascular volume data is obtained by the back projection method, and the second 3D vascular volume data corresponding to the registered bright-blood image group is used to obtain the intracranial vascular simulation 3D model. The intracranial vascular simulation 3D model can simulate the 3D intracranial vascular morphology and realize the 3D visualization of the intracranial blood vessels. It does not need doctors to restore the vascular tissue structure and disease characteristics through imagination. It is convenient for doctors to observe and analyze the morphological characteristics of the intracranial blood vessels from any interested angle and level, and can provide vivid 3D spatial information of intracranial blood vessels. It is convenient for visual observation, location and display of lesion area. It also can obtain the overall state of the intracranial blood vessels simply, quickly and intuitively in clinic for the analysis of intracranial vascular diseases.

S6, establishing a vascular 3D model with blood boundary expansion by using the registered bright-blood image group.

The blood 3D model obtained in the S5 actually represents the flow direction and regional distribution of blood. In fact, there is a vascular wall around the blood, so the blood 3D model cannot fully represent the real blood vessel.

Therefore, in the S6, the blood boundary in the registered bright-blood image can be expanded so that the expanded blood boundary can cover the range of intracranial vascular wall to form the effect of a hollow tube, and then the 3D model can be generated by the3D reconstruction method for the 2D image after expanding the blood boundary, and then the vascular 3D model closer to the real intracranial blood vessel than the blood 3D model in the S5 is obtained.

In an illustrated embodiment, the S6 may include step 61 (also referred to as S61) through step 65 (also referred to as S65):

S61, acquiring the K number of bright-blood feature images;

That is obtaining the K number of bright-blood feature images in the S32.

S62, expanding a blood boundary of each of the K number of bright-blood feature images according to an expansion operation, to obtain K number of expanded bright-blood feature images corresponding to the K number of bright-blood feature images;

Expansion operation is a kind of morphological operation. Expansion operation can fill the image void and expand the convex points of the object at the edge outward. Finally, the area of the expanded object is larger than that of the original object. The expansion operation can be recorded as $A \oplus B$, defined as $A \oplus B = \{x: B\ (x) \cap A \neq \Phi\}$, where B represents the structural element and A represents the original image. The original image A here is the bright-blood feature image. There are only two-pixel values of 0 and 255 in the bright-blood feature image. 0 corresponds to black and 255 corresponds to white.

In an illustrated embodiment, a circular box of the kernel with a radius of 1 can be used to expand the bright-blood feature image in multiple steps until the maximum gradient position is reached, so as to determine the outer wall boundary of the blood vessel, realize the segmentation of the blood vessel wall, and obtain the expanded bright-blood feature image corresponding to the bright-blood feature image. Because of the vascular wall is close to the blood and the tube wall is very thin, assuming that the expanded range is the range of the vascular wall, this step can include the region of the vascular wall near the blood as the search range of the angiography enhancement characteristics of the vascular wall.

For the specific implementation process of expansion operation, please refer to the relevant prior art and will not be repeated here.

S63, calculating a difference between each of the K number of expanded bright-blood feature images and the corresponding bright-blood feature image, to obtain K number of difference feature images corresponding to the K number of bright-blood feature images respectively;

In this step, the difference feature image obtained for each bright-blood feature image is a two-dimensional plan view similar to a hollow blood vessel. Similarly, the pixel values of the difference feature image are only 0 and 255.

S64, determining a third threshold;

In this step, a pixel value can be selected as the third threshold for all difference feature images according to the empirical value. For example, any value between 100 and 200, such as 128, can be selected as the third threshold.

S65, taking the third threshold as an input threshold of the method of marching cubes, and processing the K number of difference feature images by the method of marching cubes, to obtain the vascular 3D model with blood boundary expansion.

The method of marching cubes uses the third threshold as the input threshold, and the vascular three-dimensional model with blood boundary expansion can be obtained from the K difference feature images. The specific implementation process of the method of marching cubes will not be repeated here.

S7, establishing an angiography enhanced 3D model by using the K number of angiography enhanced images;

This step can be realized by the method of marching cubes. For details, see the S5 and the S6, which will not be repeated here.

S8, obtaining an intracranial vascular enhanced 3D model based on the blood 3D model, the vascular 3D model and the angiography enhanced 3D model.

In an illustrated embodiment, the S8 may include step 81 (also referred to as S81) and step 82 (also referred to as S82):

S81, retaining an area of the angiography enhanced 3D model overlapped with the vascular 3D model, to obtain a retained angiography enhanced 3D model;

Since the angiography enhanced 3D model obtained in the S7 does not only include the angiography enhancement of the blood vessels, and enhancement characteristics of unrelated tissues need to be excluded, the search range of the angiography enhancement characteristics of the vascular wall in the vascular three-dimensional model obtained in the S6 is used to judge whether the angiography enhanced three-dimensional model obtained in the S7 is located in the vascular wall area near the blood, that is, judge whether there is an overlap with the vascular three-dimensional model in the angiography enhanced three-dimensional model. If so, it indicates that the overlap is within the search range, and the overlap needs to be retained. Therefore, the retained angiography enhanced three-dimensional model is obtained.

S82, fusing the retained angiography enhanced 3D model with the blood 3D model, to obtain the enhanced 3D model of intracranial angiography.

By fusing the retained angiography enhanced 3d model representing angiography enhancement with the blood 3D model representing blood information, we can visually display the vascular wall with obvious angiography enhancement, and clearly see which part of intracranial blood vessels has the most obvious angiography enhancement effect, then atherosclerotic or vulnerable plaque may appear in this area.

the angiography enhanced quantitative analysis can be obtained in the intracranial vascular enhanced 3D model. Specifically, the plaque enhancement index CE can be obtained for any point on the vascular wall in the intracranial vascular enhanced 3D model, which is defined as:

$$CE = \frac{S_{postBBMR} - S_{preBBMR}}{S_{preBBMR}}; \qquad (4)$$

where $S_{preBBMR}$ and $S_{postBBMR}$ are respectively signal intensities of the black-blood image and the angiography enhanced black-blood image.

It can be understood by those skilled in the art that $S_{preBBMR}$ and $S_{postBBMR}$ are the information carried in the images after photographing the black-blood image and the angiography enhanced black-blood image respectively. The embodiment of the disclosure uses the above information to obtain the plaque enhancement index CE of each point along the edge of the intracranial vascular wall and embody it in the intracranial vascular enhanced 3D model, which can facilitate doctors to obtain more detailed vascular information. Specifically, when CE is greater than a plaque threshold, such as 0.5, it indicates that there is a plaque on the vascular wall. Therefore, by measuring the plaque enhancement index of the area of the vascular wall, it is helpful to identify the responsible intracranial artery plaque, and can provide valuable diagnostic auxiliary information.

The fusion technology of two three-dimensional models can be realized by using the existing technology, which will not be repeated here.

S9, obtaining values of target parameters representing degrees of vascular stenosis of respective vascular segments of the intracranial vascular enhanced 3D model, and marking the intracranial vascular enhanced 3D model by using the values of the target parameters of the respective vascular segments, to obtain an intracranial vascular lesion recognition model.

In an illustrated embodiment, the S9 may include step 91 (also referred to as S91) through step 94 (also referred to as S94):

S91, segmenting each of the vascular segments of the intracranial vessel enhanced 3D model from preset three directions to obtain 2D cross-sectional images respectively corresponding to the three preset directions.

In this step, the blood vessels in the intracranial vascular enhanced 3D model can be divided first, and each of the vascular segments can be segmented from the preset three directions to obtain the 2D cross-sectional image of each direction.

Among them, the preset three directions include axial, coronal and sagittal directions.

S92, performing corrosion operations on the vascular segments of the 2D cross-sectional images corresponding to the three preset directions, and recording a target corrosion times when the vascular segments are corroded until a single pixel.

In the embodiment of the disclosure, the thickness of the blood vessel is estimated according to the number of times when the corresponding part of the blood vessel reaches a single pixel in the corrosion operation.

In the step S92, the corrosion operation is performed on the blood vessels of the 2D cross-sectional image in the axial direction, and the corresponding target corrosion times $n_1$ when the blood vessels of the 2D cross-sectional image in the axial direction are corroded to a single pixel are recorded. The corrosion operation is performed on the blood vessels of the 2D cross-sectional image in the coronal direction, and the corresponding target corrosion times $n_2$ when the blood vessels of the 2D cross-sectional image in the coronal direction are corroded to a single pixel are recorded. The corrosion operation is performed on the blood vessels of 2D cross-sectional image in the sagittal direction, and the corresponding target corrosion times $n_3$ when the blood vessels of the 2D cross-sectional image in the sagittal direction are corroded to a single pixel are recorded.

S93, obtaining the value of the target parameter representing the degree of vascular stenosis of each of the vascular segments according to the target corrosion times of the vascular segment respectively corresponding to the three preset directions;

In an illustrated embodiment, the target parameters include stenosis rate and/or flatness. Those skilled in the art can understand that both parameters can characterize the degree of vascular stenosis.

When the target parameter includes the stenosis rate, the S93 may include:

obtaining the value of the stenosis rate of the segment of blood vessel according to $n_1$, $n_2$, $n_3$ by using a stenosis rate formula of blood vessel; and the stenosis rate formula is defined as:

$$\text{stenosis rate} = \frac{n_1 + n_2 + n_3}{3} \times \text{resolution}; \quad (5)$$

where the resolution is the resolution of the 2D cross-sectional image in each direction (the resolution of the 2D cross-sectional image in three preset directions is the same). The smaller the value of the stenosis rate, the narrower the blood vessel.

When the target parameter includes the flatness, the S93 may include:

obtaining the value of the flatness of the segment of blood vessel according to $n_1$, $n_2$, $n_3$ by using a flatness formula of the blood vessel; and the flatness formula is defined as:

$$\text{flatness} = \frac{\sqrt{(n_1 - n_2)^2 + (n_2 - n_3)^2 + (n_3 - n_1)^2}}{\sqrt{2(n_1^2 + n_2^2 + n_3^2)}}; \quad (6)$$

where the larger the value of the flatness, the narrower the blood vessel.

S94, marking the intracranial vascular enhanced 3D model by using the value of the target parameter of each of the vascular segments to obtain the intracranial vascular lesion recognition model.

Through the above steps, the value of the target parameter of each segment of blood vessels can be obtained, and then these values of each segment of blood vessels can be marked on the angiography enhanced 3D model to obtain the intracranial vascular lesion recognition model. That is, the value of the target parameter of each point is embedded in the intracranial vascular lesion recognition model, so that the value of the target parameter of each point can be extracted and displayed when necessary, so that the doctor can timely obtain the data of the degree of vascular stenosis at each position when observing the overall three-dimensional vascular state. For example, when the intracranial vascular lesion recognition model is displayed on the computer display screen, the stenosis rate and/or the flatness of the mouse position point can be displayed in the blank area of the model.

In order to facilitate visual display, different values can be marked with different colors on the angiography enhanced 3D model to obtain the intracranial vascular lesion recognition model. For example, for the values of the stenosis rate from small to large, multiple colors from light to deep can be marked. For the values of the flatness, there may be only two kinds of values, so two colors corresponding marks can be used to distinguish the stenosis rate. The color display of different tones can more intuitively show the degree of vascular stenosis, which is convenient to attract the attention of doctors.

Figures 5A, 5B:
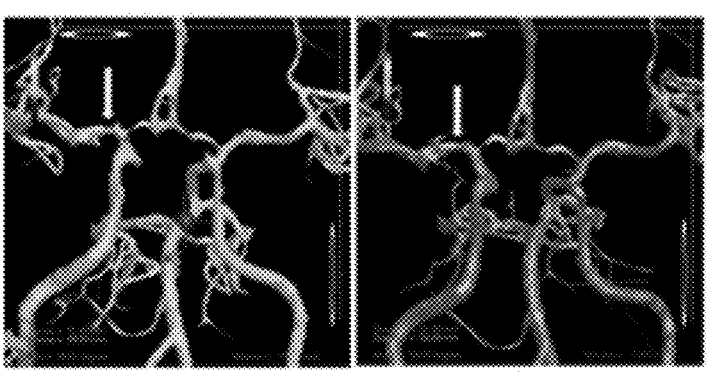
FIG. 5A shows effect of marking an intracranial vascular lesion recognition model by using a stenosis rate according to an embodiment of the disclosure.
FIG. 5B shows effect of marking the intracranial vascular lesion recognition model by using a flatness according to the embodiment of the disclosure.

FIGS. 5A-5B show effects of an intracranial vascular lesion recognition model according to the embodiment of the disclosure. Specifically, FIG. 5A shows effect of marking the intracranial vascular lesion recognition model by using the stenosis rate in the embodiment of disclosure, and FIG. 5B shows effect of marking the intracranial vascular lesion recognition model using the flatness in the embodiment of disclosure. In practice, different colors are displayed on the model, which can distinguish the degree of stenosis. For example, the thinnest part of the blood vessel is warm color, the narrowest part is red, the thickest part is cold color, and the coarsest part is green, etc., the white arrow shows the sudden stenosis of intracranial blood vessels, and the color display of different tones can more intuitively show the vascular stenosis. The effect of gray processing is shown in the drawings, and the color is not shown.

Figure 6:
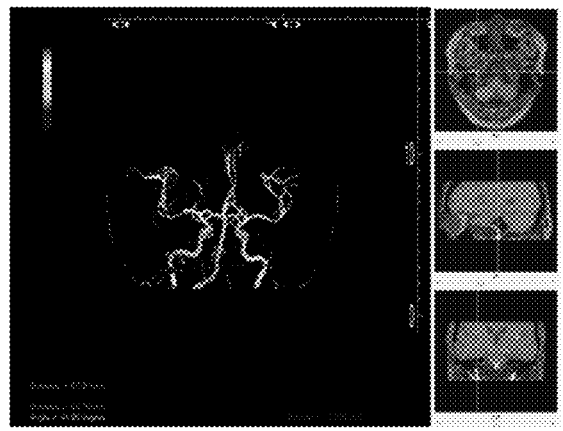
FIG. 6 is a display effect diagram of the intracranial vascular lesion recognition model and cross-sectional images according to the embodiment of the disclosure.

Furthermore, because doctors are used to observing the two-dimensional medical image of the cutting plane, the embodiment of the disclosure can provide the simulated three-dimensional vascular stenosis analysis model and provide the two-dimensional cross-sectional images of three directions, that is, the coronal, sagittal, and axial images of the current point corresponding to each point in the simulated three-dimensional vascular stenosis analysis model can be displayed. Referring to FIG. 6, FIG. 6 is a display effect diagram of the intracranial vascular lesion recognition model and cross-sectional images according to the embodiment of the disclosure. In FIG. 6, there may be vascular stenosis in the warm colors of the blood vessels, but there is no obvious vascular stenosis in the cold colors of the blood vessels, and the three two-dimensional images on the right of the image are the axial plane, sagittal plane and coronal plane where the current point is located from top to bottom. When displaying the simulated three-dimensional vascular stenosis analysis model, points in three colors such as red, green and blue can also be used to realize the functions of two points ranging and three points measuring angles, which are displayed at the lower left of the display screen, and the volume size of the currently selected model is displayed at the lower right of the display screen, so that doctors can obtain more detailed data of intracranial blood vessels.

In the solution provided by the embodiment of the disclosure, firstly, the bright-blood image and the enhanced black-blood image scanned by magnetic resonance angiography technology are registered by using the registration method based on mutual information and image pyramid, which can improve the registration efficiency and improve the registration accuracy layer by layer from low resolution to high resolution. Through the above image registration, the bright-blood image and the enhanced black-blood image can be unified in the same coordinate system. Secondly, using the registered bright-blood image to eliminate the flowing void artifact of the enhanced black-blood image can display more accurate and comprehensive vascular information. The solution provided by the embodiment of the disclosure is to eliminate the flowing void artifact from the perspective of image post-processing without using new imaging technology, imaging mode or pulse sequence. Therefore, the flowing void artifact can be eliminated simply, accurately and quickly, and can be well popularized in clinical application. Thirdly, the blood 3D model is established by using the registered bright-blood image, the vascular 3D model with blood boundary expansion is established by using the registered bright-blood image, and the angiography enhanced 3D model is obtained by subtracting the artifact-elimination enhanced black-blood image and black-blood image. Based on the blood 3D model, the vascular 3D model and the angiography enhanced 3D model, the angiography enhanced 3D model corresponding to the vascular wall with angiographic enhancement effect is obtained. Finally, the values of the target parameters representing the degrees of vascular stenosis in the intracranial angiography enhanced 3D model are marked to obtain the intracranial vascular lesion recognition model. The intracranial vascular lesion recognition model realizes the three-dimensional visualization of intracranial blood vessels. It does not need doctors to restore the tissue structure and disease characteristics of intracranial blood vessels through imagination. It can provide vivid three-dimensional spatial information of intracranial blood vessels, facilitate intuitive observation, and locate and display the narrow lesion area. In clinical application, it can simply, quickly and intuitively obtain the real information of intracranial blood vessels and the analysis data of the degree of intracranial vascular stenosis.

The implementation process and implementation effect of the intracranial vascular lesion recognition method based on transfer learning provided by the embodiment of the disclosure are described in detail below. The implementation process can include the following step 1 through step 9:

step 1: obtaining a bright-blood image group, a black-blood image group and an enhanced black-blood image group of an intracranial vascular site. Specifically, the bright-blood image group, the black-blood image group and the enhanced black-blood image group respectively comprise K number of bright-blood images, K number of black-blood images and K number of enhanced black-blood images, the K number of bright-blood images of the bright-blood image group, the K number of black-blood images of the black-blood image group and the K number of enhanced black-blood images of the enhanced black-blood image group are corresponded one by one, and K is a natural number greater than 2.

Step 2: performing an image registration to each of the K number of bright-blood images by using a corresponding one of the K number of enhanced black-blood images of the enhanced black-blood image group as a reference through a registration method based on mutual information and image pyramid, to obtain a registered bright-blood image group comprising K number of registered bright-blood images.

The step 2 may include:

(1), preprocessing each of the K number of bright-blood images and the corresponding one of the K number of enhanced black-blood images to obtain a first bright-blood image and a first black-blood image; and the preprocessing can be divided into two main steps:

(i) pre-registration:

Because the intracranial blood vessel can be regarded as a rigid body, the rigid body transformation is selected as the coordinate transformation method in this step. For the specific pre-registration process, please refer to the step S211, which will not be repeated here.

The embodiment of the disclosure carries out a simulation experiment on the image interpolation method of the bright-blood image, first reduces the original image by 50%, and then uses different interpolation algorithms to obtain the effect image with the same size as the original image, and compares it with the original image. The data shown in Table 1 are the mean values of the results of 100 repeated interpolation operations. A total of five evaluation indexes are set, namely a root mean square error (RMSE), a peak signal-to-noise ratio (PSNR), a normalized cross-correlation coefficient (NCC), a normalized mutual information (NMI) and a time-consuming (Time). The smaller RMSE, the more accurate registration, and the higher values of PSNR, NCC and NMI, the more accurate registration. From the overall experimental data, the accuracy of the bicubic interpolation is obviously better than the nearest neighbor interpolation and the bilinear interpolation. Although the interpolation time of the bicubic interpolation is slower than the previous two methods, the 100 interpolation operations are only 0.1 seconds longer than the fastest nearest neighbor interpolation, that is, each operation is only 0.001 seconds slower. Therefore, on balance, the embodiment of the disclosure adopts the bicubic interpolation with high image quality.

TABLE 1

Analysis of image interpolation results

| Interpolation method | Evaluation index | | | | |
| --- | --- | --- | --- | --- | --- |
| | RMSE | PSNR | NCC | NMI | Time/s |
| Nearest neighbor interpolation | 4.200 | 35.665 | 0.981 | 0.46 | 0.098 |
| bilinear interpolation | 4.086 | 35.906 | 0.990 | 0.45 | 0.128 |
| bicubic interpolation | 2.990 | 38.618 | 0.995 | 0.91 | 0.198 |

In the embodiment of the disclosure, the intracranial blood vessel can be regarded as a rigid body with almost no deformation, which is different from that organs such as heart or lung will change with the movement of human breathing. Therefore, compared with other types of blood vessels, mutual information is more suitable to be selected as the similarity measure to achieve more accurate registration effect.

In the experiment, in the image using (1+1)-ES optimizer, the registration result is accurate, and the shadow parts that do not overlap in the image disappear completely. The data shown in Table 2 are the three evaluation indexes of registration results, namely NMI, NCC and Time. From the experimental result image, the registration image effect using the (1+1)-ES optimizer is clearer and better than the gradient descent optimizer; From the experimental data, the three evaluation indexes show the good performance of the (1+1)-ES optimizer. Therefore, the embodiment of the disclosure uses (1+1)-ES as the search strategy.

TABLE 2

Analysis of results under different search strategies

| Search strategy | Evaluation index | | |
|---|---|---|---|
| | NMI$^a$ | NCC$^a$ | Time$^a$/s |
| Gradient descent optimizer | 0.14 ± 0.02 | 2179.81 ± 597.31 | 1.11 ± 0.44 |
| (1 + 1)-ES optimizer | 0.17 ± 0.01 | 2147.34 ± 586.85 | 0.70 ± 0.07 |

The value in a is the mean±mean square error of the evaluation index based on the registration of 160 bright-blood images and 160 enhanced black-blood images Referring to FIG. 7, FIG. 7 shows a result of intracranial vascular magnetic resonance images after pre-registration according to the embodiment of the disclosure. The left image of FIG. 7 shows the first bright-blood image after the pre-registration, in which the interpolation method adopts the bicubic interpolation; the middle image shows the enhanced black-blood image, both of which are the coronal planes; the right image shows the effect after direct superposition of the first bright-blood image after the pre-registration and the enhanced black-blood image. The right image shows that although the bright-blood image and the enhanced black-blood image under the current imaging layer can be observed under the same coronal plane after the pre-registration, they still do not coincide, so subsequent accurate registration of the image is required.

(ii) Unified scanning area:

The content of an area same as a scanning range of the first bright-blood image is extracted from the enhanced black-blood image to thereby form the first black-blood image. For the specific process, please refer to the step S212, which will not be repeated here.

Referring to FIG. 8, FIG. 8 shows an area to be registered of the intracranial vascular magnetic resonance images according to the embodiment of the disclosure, in which the left image is the first bright-blood image after the pre-registration, the right image is the enhanced black-blood image, and the rectangular box is the area to be extracted in the enhanced black-blood image. This area includes the common scanning range of the bright-blood sequence and the black-blood sequence in the intracranial vascular magnetic resonance images. By determining the area to be extracted, it can pay more attention to useful information more quickly.

(2), performing an image registration to each of the first bright-blood image and the first black-blood image by using a registration method based on mutual information and image pyramid after the preprocessing. For details, refer to the relevant contents of steps S22~S27 above. Specifically include:

(a), obtaining a bright-blood Gaussian pyramid according to the first bright-blood image and a black-blood Gaussian pyramid according to the first black-blood image based on down-sampling processing.

Among them, each of the bright-blood Gaussian pyramid and the black-blood Gaussian pyramid includes four images whose resolution decreases from bottom to top; refer to the step S22 above for the generation process of the bright-blood Gaussian pyramid and the black-blood Gaussian pyramid, which will not be repeated here. As shown in FIGS. 9A-9B, FIGS. 9A-9B are schematic diagrams of a bright-blood Gaussian pyramid and a black-blood Gaussian pyramid of the intracranial vascular magnetic resonance images respectively according to the embodiment of the disclosure.

These resolutions gradually decrease, which come from the combination of images with different resolutions of the same image, which are arranged like a pyramid, so they are called image pyramid, in which the image with the highest resolution is located at the bottom of the pyramid and the image with the lowest resolution is located at the top of the pyramid. In computer vision, images with different resolutions exactly simulate an image observed by human eyes at different distances. In image information processing, multi-resolution images are easier to obtain the essential characteristics of images than traditional single resolution images.

(b), obtaining a bright-blood Laplace pyramid according to the bright-blood Gaussian pyramid and a black-blood Laplace pyramid according to the black-blood Gaussian pyramid based on up-sampling processing.

Among them, each of the bright-blood Laplacian pyramid and the black-blood Laplacian pyramid includes three images whose resolution decreases from bottom to top. For the generation process of the bright-blood Laplacian pyramid and the black-blood Laplacian pyramid, refer to the step S23 above, which will not be repeated here. As shown in FIGS. 9C-9D, FIGS. 9C-9D are schematic diagrams of a bright-blood Laplacian pyramid and a black-blood Laplacian pyramid of the intracranial vascular magnetic resonance images respectively according to the embodiment of the disclosure. The image display uses gamma correction to achieve clearer effect, and the gamma value is 0.5.

(c), registering the images in each layer of the bright-blood Laplacian pyramid with the image in a corresponding layer of the black-blood Laplacian pyramid to obtain a registered bright-blood Laplacian pyramid.

In this step, the image in the black-blood Laplacian pyramid is used as the reference image and the image in the bright-blood Laplacian pyramid is used as the floating image, the enhanced black-blood image of each layer and the bright-blood image of the corresponding layer are registered respectively, mutual information is used as the similarity measure of the two images, and the (1+1)-ES optimizer is selected as the search strategy. After the coordinate transformation of each image registration, mutual information of the two images is calculated iteratively until mutual information reaches the maximum and the image registration is completed. For the specific process, refer to the step S24 above, which will not be repeated here.

Figures 10A, 10B, 10C:
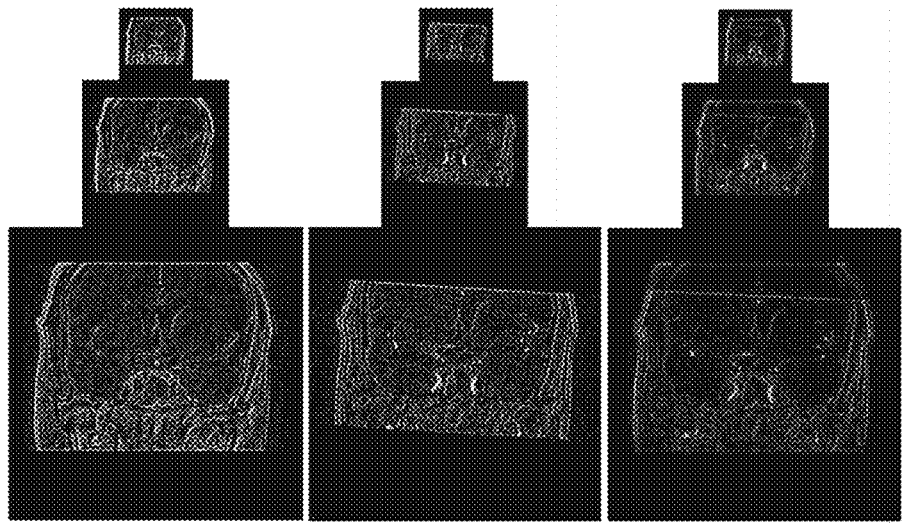
FIGS. 10A-10C show registration results of Laplacian pyramid images of the intracranial vascular magnetic resonance images according to the embodiment of the disclosure.

The results are shown in FIGS. 10A-10C. FIGS. 10A-10C show registration results of the Laplacian pyramid images of intracranial vascular magnetic resonance images according to the embodiment of the disclosure. FIG. 10A is the reference image in the black-blood Laplacian pyramid, FIG. 10B is the registered image in the bright-blood Laplacian pyramid, and FIG. 10C is the effect picture after the images of FIG. 10A and FIG. 10C are directly superimposed. The superimposed image is displayed by the montage effect, using the pseudo color transparent processing to the enhance black-blood image and the bright-blood image, in which purple is the enhanced black-blood Laplacian pyramid image and green is the bright-blood Laplacian pyramid image (FIGS. 10A-10C are the gray processed images of the original images, and the color is not shown).

(d), registering the images in respective layers of the bright-blood Gaussian pyramid with the images in corresponding layers of the black-blood Gaussian pyramid respectively from top to bottom by using the registered bright-blood Laplace pyramid as superposition information to obtain a registered bright-blood Gaussian pyramid.

Figure 11:
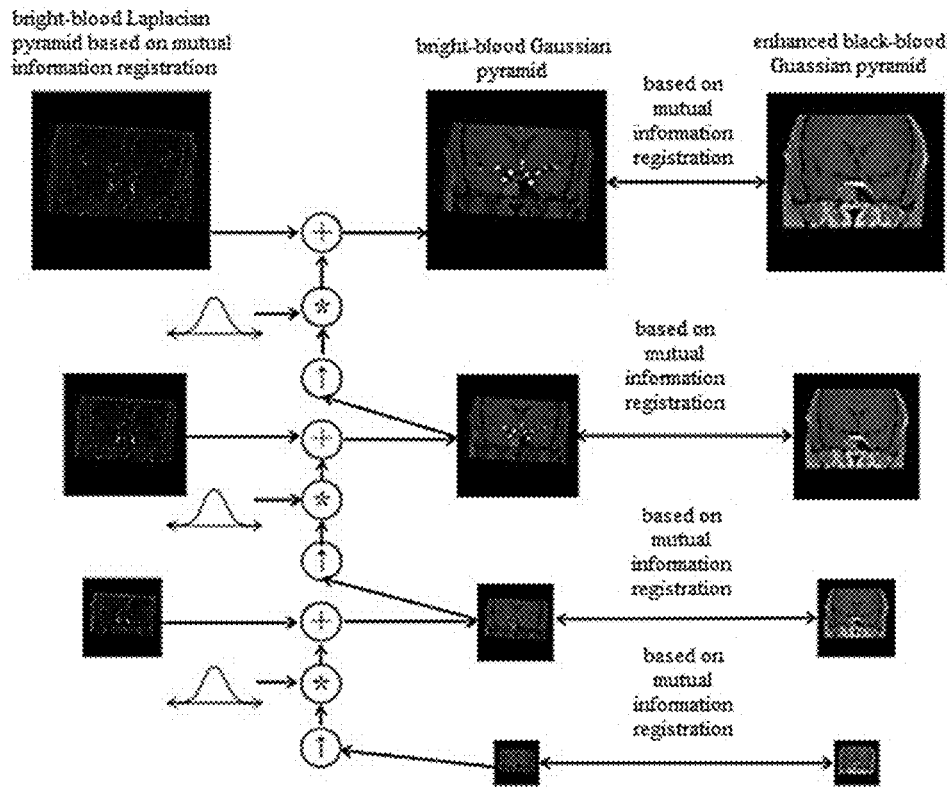
FIG. 11 a schematic diagram of steps of registration based on mutual information of Gaussian pyramid images of the intracranial vascular magnetic resonance images according to the embodiment of the disclosure.

For this step, refer to S25 above. The specific steps of Gaussian pyramid image registration based on mutual information are shown in FIG. 11. FIG. 11 is a schematic diagram of steps of registration based on mutual information of Gaussian pyramid images of intracranial vascular magnetic resonance images according to the embodiment of the disclosure. Firstly, performing the registration based on mutual information to the low-resolution black-blood Gaussian image on the top layer and the low-resolution bright-blood Gaussian image on the top layer; then, performing the up-sampling operation to the registered bright-blood Gaussian image and adding it to the registered bright-blood Laplacian image of the corresponding layer that retains the high-frequency information as the bright-blood Gaussian image of the next layer; then, the bright-blood Gaussian image obtained by the above operation is used as the input image, and then it is registered with the black-blood Gaussian image of the corresponding layer, repeating the above operations until the high-resolution registration of the Gaussian pyramid image of the bottom layer is completed.

In the registration of the Gaussian pyramid image based on mutual information, it is necessary to register each layer of the bright-blood Gaussian image and the black-blood Gaussian image with the normalized mutual information as the similarity measure, and calculate the NMI of the two images through cyclic iteration until the NMI reaches the maximum. When the times of the iterations is too small, the accurate image registration cannot be completed, but when the times of the iterations is too large, the amount of calculation will increase sharply. FIG. 12 shows the normalized mutual information under different iterations of the embodiment of the disclosure. When the first layer image, that is, the image with the highest-resolution of the bottom layer in the Gaussian pyramid, reaches the maximum NMI value and the data is stable, the iteration is stopped.

In addition, in order to verify effectiveness and practicability of the registration method based on mutual information and image pyramid (hereinafter referred to as mutual information pyramid method) in the embodiment of the disclosure, comparative experiments were also carried out. A total of intracranial vascular magnetic resonance images of five patients were used, in which the enhanced black-blood images and bright-blood images of patients A, B, C and D are 160 respectively, and the enhanced black-blood images and the bright-blood images of patient E are 150 respectively. At the same time, the algorithm that only uses the orientation label information of DICOM image for registration and the registration algorithm based on mutual information measurement are selected to compare with mutual information pyramid method in the embodiment of the disclosure. The algorithm based on mutual information measurement is to find the best transformation between the reference image and the floating image through the multi parameter optimization method, so as to maximize mutual information value of the two images, and image pyramid algorithm is not used in the algorithm based on mutual information measurement.

Figure 13D:
Figure 13E:
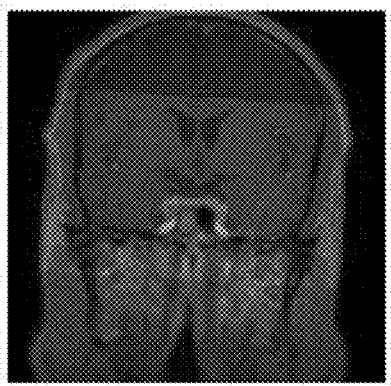

The experimental platform is Matlab R2016b. According to registration results of the experimental images, the combination of qualitative analysis and quantitative analysis is adopted. In terms of the qualitative analysis, due to the large gray difference between multimodal medical images, the difference image obtained by subtracting the registered image from the reference image cannot effectively reflect the registration result of the multimodal medical images. Therefore, the embodiment of the disclosure overlaps the registered image with the reference image, the color overlapping image which can reflect the alignment degree of the registered image and the reference image is obtained. The registration effect of the multi-modal registration algorithm is qualitatively analyzed through the color overlapping image, FIGS. 13A-10E show the registration results of the magnetic resonance images of multimodal intracranial blood vessels, and FIG. 13A through FIG. 13E show the registration results of intracranial vascular magnetic resonance images of various registration methods including mutual information pyramid method. FIG. 13A is the reference image; FIG. 13B is the floating image; FIG. 13C is the overlapping image based on image orientation label information; FIG. 13D is the overlapping image based on mutual information measurement; FIG. 13E is the overlapping image of mutual information pyramid method according to the embodiment of the disclosure. FIG. 13A through FIG. 13E are gray-scale images of the original images, and the color is not shown. In terms of the quantitative analysis, since the evaluation indexes including the root mean square error (RMSE) and the peak signal-to-noise ratio (PSNR) are not suitable for evaluating images with large gray changes, in order to better evaluate the registration results of the multimodal medical images, the normalized cross-correlation coefficient (NCC) and the normalized mutual information (NMI) are used as the evaluation indexes, the larger values of the normalized cross-correlation coefficient and the normalized mutual information, the higher accuracy of the image registration. Table 3 shows the result analysis of the evaluation indexes of different registration algorithms.

TABLE 3

Result Analysis of different registration methods (also referred as algorithms)

| Data of patient | registration algorithm | NCC$^a$ | NMI$^a$ |
| --- | --- | --- | --- |
| patient A | based on image orientation label information | 0.57 ± 0.08 | 0.14 ± 0.01 |
| | based on mutual information measurement | 0.56 ± 0.05 | 0.13 ± 0.01 |
| | mutual information pyramid method | 0.59 ± 0.08 | 0.17 ± 0.01 |
| patient B | based on image orientation label information | 0.68 ± 0.07 | 0.21 ± 0.02 |
| | based on mutual information measurement | 0.57 ± 0.05 | 0.18 ± 0.01 |
| | mutual information pyramid method | 0.70 ± 0.06 | 0.22 ± 0.01 |
| patient C | based on image orientation label information | 0.57 ± 0.05 | 0.14 ± 0.01 |
| | based on mutual information measurement | 0.51 ± 0.07 | 0.13 ± 0.01 |
| | mutual information pyramid method | 0.64 ± 0.05 | 0.17 ± 0.01 |
| patient D | based on image orientation label information | 0.69 ± 0.04 | 0.18 ± 0.01 |
| | based on mutual information measurement | 0.49 ± 0.04 | 0.15 ± 0.01 |
| | mutual information pyramid method | 0.71 ± 0.04 | 0.19 ± 0.01 |
| patient E | based on image orientation label information | 0.63 ± 0.08 | 0.16 ± 0.01 |
| | based on mutual information measurement | 0.53 ± 0.07 | 0.15 ± 0.01 |
| | mutual information pyramid method | 0.66 ± 0.08 | 0.17 ± 0.01 | where the value of a in the Table 3 is the mean value±mean square error of the evaluation indexes of multiple image registration based on the patient.

The qualitative analysis: it is obvious from the overlapping images from FIG. 13C through FIG. 13E that the method based on mutual information measurement has a large registration offset. The analysis reason may be that it is easy to fall into the local optimal value rather than the global optimal value only using the method based on mutual information measurement; The registration effect based on image orientation label information is also poor, and some images do not overlap; The registration image effect of mutual information pyramid method is good, the image display is clearer, and the images are almost completely overlapped.

The quantitative analysis: it can be seen from the Table 3 that from the two evaluation indexes of NCC and NMI, mutual information pyramid method of the embodiment of the disclosure improves the registration accuracy compared with the registration algorithm using only the orientation label information of DICOM image and the registration algorithm based on mutual information measurement, it shows that the registration method based on mutual information and image pyramid proposed in the embodiment of the disclosure can well process the registration of magnetic resonance images of multimodal intracranial blood vessel.

(e), obtaining K number of registered bright-blood images corresponding to the K number of bright-blood images respectively based on the registered bright-blood Gaussian pyramid;

Specifically, the bottom image in the registered bright-blood Gaussian pyramid is obtained as the registered bright-blood image, and the registered bright-blood image and the corresponding enhanced black-blood image are taken as the registered image pair.

(f), obtaining the registered bright-blood image group according to the K number of bright-blood images corresponding to the K number of registered bright-blood images.

In the embodiment of the disclosure, the image registration method based on mutual information and image pyramid is used to register the magnetic resonance bright-blood image and enhanced black-blood image. In the registration process, not only the correlation of gray information is considered, but also the Gaussian pyramid is used to improve the registration efficiency, make the image from low resolution to high resolution, and improve the registration accuracy layer by layer.

Step 3, performing an elimination operation of flowing void artifact to the K number of enhanced black-blood images of the enhanced black-blood image group by using the registered bright-blood image group, to obtain an artifact-elimination enhanced black-blood image group comprising K number of object enhanced black-blood images; and referring to the step S3 above for details.

Figure 14:
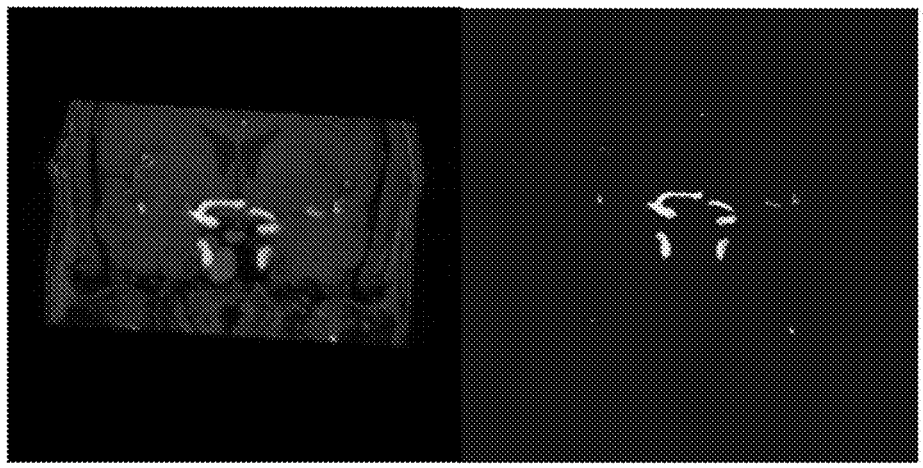
FIG. 14 shows a result of gray-scale linear transformation according to an embodiment of the disclosure.

Firstly, for each registered bright-blood image, the gray-scale linear transformation is used to improve the contrast of the registered bright-blood image, and the contrast enhanced bright-blood image is obtained. As shown in FIG. 14, FIG. 14 shows a result of gray-scale linear transformation according to an embodiment of the disclosure, in which the left image is the registered bright-blood image, and the right image is the result image after gray-scale linear transformation. It can be seen that the contrast of the blood part in the right image is significantly enhanced compared with the surrounding pixels.

Figure 15:
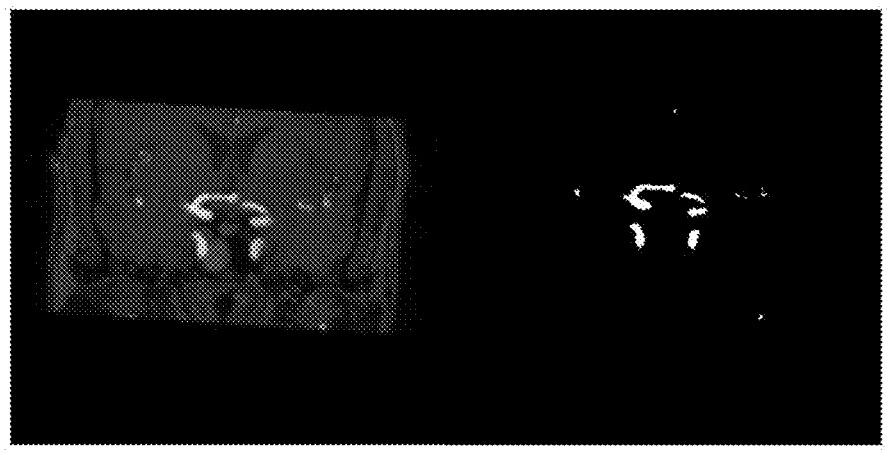
FIG. 15 shows a result of image binarization according to an embodiment of the disclosure.

Secondly, the blood information is extracted from the contrast-enhanced bright-blood image to obtain the bright-blood feature image;

The method of maximum interclass variance method OTSU is adopted in this step, and a result are shown in FIG. 15. FIG. 15 shows a result of the image binarization of the embodiment of the disclosure, in which the left image is the contrast-enhanced bright-blood image, and the right image is the blood information after threshold extraction. It can be seen that the bright part in the right image is only information related to the blood.

Thirdly, the bright-blood feature map is fused with the enhanced black-blood image corresponding to the registered bright-blood image according to the preset fusion formula to obtain the object enhanced black-blood image with flowing void artifact elimination corresponding to the enhanced black-blood image.

Figure 16:
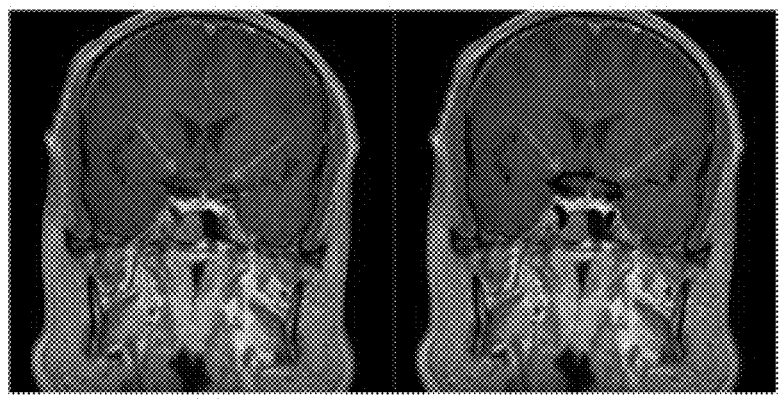
FIG. 16 shows a result of eliminating flow void artifacts for intracranial blood vessels according to an embodiment of the disclosure.

The specific steps will not be repeated, and the comparison results can be seen in FIG. 16. FIG. 16 shows the results of eliminating the flowing void artifact obtained by different methods for the intracranial blood vessel in the embodiment of the disclosure, in which the image on the left is the original image of the enhanced black-blood image, and the image on the right is the enhanced black-blood image after the elimination of the flowing void artifact. The flowing void artifact appears at the arrow, and it can be seen that the elimination effect of the flowing void artifact is more obvious.

Finally, the artifact-elimination enhanced black-blood image group is obtained according to the K number of object enhanced black-blood images corresponding to the K number of enhanced black-blood images.

Step 4, performing a subtraction operation between each of the K number of object enhanced black-blood images of the artifact-elimination enhanced black-blood image group and a corresponding one of the K number of black-blood images of the black-blood image group, to obtain K number of angiography enhanced images;

Step 5, establishing a blood 3D model by using the registered bright-blood image group, based on transfer learning;

Step 6, establishing a vascular 3D model with blood boundary expansion by using the registered bright-blood image group;

Step 7, establishing an angiography enhanced 3D model by using the K number of angiography enhanced images;

Step 8, obtaining an intracranial vascular enhanced 3D model based on the blood 3D model, the vascular 3D model and the angiography enhanced 3D model; and Step 9, obtaining values of target parameters representing degrees of vascular stenosis of respective vascular segments of the intracranial vascular enhanced 3D model, and marking the intracranial vascular enhanced 3D model by using the values of the target parameters of the respective vascular segments, to obtain an intracranial vascular lesion recognition model.

The specific process of steps 4 through 9 will not be repeated.

Figure 17:
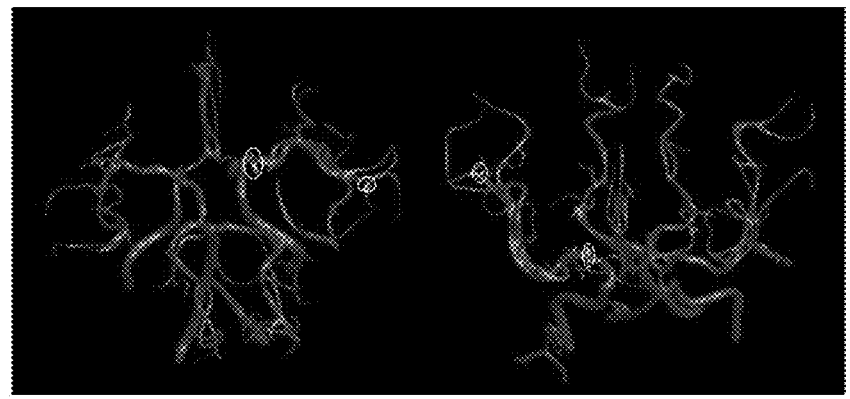
FIG. 17 shows effect of an intracranial vascular enhanced 3D model.

Refer to FIG. 17, FIG. 17 shows effect of the intracranial vascular enhanced 3D model in the embodiment of the disclosure. The bright part in the white coil in the attached drawings of the specification is the vascular site with angiography enhancement, that is, here may be intracranial atherosclerosis or vulnerable plaque, and the rest is the vascular site without angiography enhancement. In practice, different colors can be used to distinguish in FIG. 17. For example, blue is the vascular site without angiography enhancement, and red is the vascular site with angiography enhancement. The intracranial vascular enhanced 3D model can realize the basic functions of rotation, magnification and reduction, so as to help doctors locate the focus area and make more accurate judgment.

In the solution provided by the embodiment of the disclosure, the three-dimensional visualization of intracranial blood vessels is realized without the doctor's imagination to restore the vascular tissue structure and disease characteristics, which can facilitate the doctor to observe and analyze the vascular morphological characteristics from any interested angle and level, and can provide realistic three-dimensional spatial information of blood vessels. It is convenient to visually display the vessel wall with obvious contrast enhancement, and to locate and display the focus area. In clinical application, it can simply and quickly obtain the real information of blood vessels for the analysis of vascular diseases.

What is claimed is:

1. A recognition method of intracranial vascular lesions based on transfer learning, comprising:
    obtaining a bright-blood image group, a black-blood image group and an enhanced black-blood image group of an intracranial vascular site; wherein the bright-blood image group, the black-blood image group and the enhanced black-blood image group respectively comprise K number of bright-blood images, K number of black-blood images and K number of enhanced black-blood images, the K number of bright-blood images of the bright-blood image group, the K number of black-blood images of the black-blood image group and the K number of enhanced black-blood images of the enhanced black-blood image group are corresponded one by one, and K is a natural number greater than 2;
    performing an image registration to each of the K number of bright-blood images by using a corresponding one of the K number of enhanced black-blood images of the enhanced black-blood image group as a reference through a registration method based on mutual information and image pyramid, to obtain a registered bright-blood image group comprising K number of registered bright-blood images;
    performing an elimination operation of flowing void artifact to the K number of enhanced black-blood images of the enhanced black-blood image group by using the registered bright-blood image group, to obtain an artifact-elimination enhanced black-blood image group comprising K number of object enhanced black-blood images;
    performing a subtraction operation between each of the K number of object enhanced black-blood images of the artifact-elimination enhanced black-blood image group and a corresponding one of the K number of black-blood images of the black-blood image group, to obtain K number of angiography enhanced images;
    establishing a blood three-dimensional (3D) model by using the registered bright-blood image group, based on transfer learning;
    establishing a vascular 3D model with blood boundary expansion by using the registered bright-blood image group;
    establishing an angiography enhanced 3D model by using the K number of angiography enhanced images;
    obtaining an intracranial vascular enhanced 3D model based on the blood 3D model, the vascular 3D model and the angiography enhanced 3D model; and
    obtaining values of target parameters representing degrees of vascular stenosis of respective vascular segments of the intracranial vascular enhanced 3D model, and marking the intracranial vascular enhanced 3D model by using the values of the target parameters of the respective vascular segments, to obtain an intracranial vascular lesion recognition model.

2. The recognition method according to claim 1, wherein the performing an image registration to each of the K number of bright-blood images by using a corresponding one of the K number of enhanced black-blood images of the enhanced black-blood image group as a reference through a registration method based on mutual information and image pyramid, to obtain a registered bright-blood image group comprising K number of registered bright-blood images, comprises:
    preprocessing each of the K number of bright-blood images and the corresponding one of the K number of enhanced black-blood images to obtain a first bright-blood image and a first black-blood image;
    obtaining a bright-blood Gaussian pyramid according to the first bright-blood image and a black-blood Gaussian pyramid according to the first black-blood image based on down-sampling processing; wherein each of the bright-blood Gaussian pyramid and the black-blood Gaussian pyramid comprises m number of images with resolution decreased gradually from bottom to top, and m is a natural number greater than 3;
    obtaining a bright-blood Laplace pyramid according to the bright-blood Gaussian pyramid and a black-blood Laplace pyramid according to the black-blood Gaussian pyramid based on up-sampling processing; wherein each of the bright-blood Laplacian pyramid and the black-blood Laplacian pyramid comprises m−1 number of images with resolution decreased gradually from bottom to top;
    registering the images in each layer of the bright-blood Laplacian pyramid with the image in a corresponding layer of the black-blood Laplacian pyramid to obtain a registered bright-blood Laplacian pyramid;
    registering the images in respective layers of the bright-blood Gaussian pyramid with the images in corresponding layers of the black-blood Gaussian pyramid respectively from top to bottom by using the registered bright-blood Laplace pyramid as superposition information to obtain a registered bright-blood Gaussian pyramid;
    obtaining K number of registered bright-blood images corresponding to the K number of bright-blood images respectively based on the registered bright-blood Gaussian pyramid; and
    obtaining the registered bright-blood image group according to the K number of bright-blood images corresponding to the K number of registered bright-blood images.

3. The recognition method according to claim 2, wherein the preprocessing each of the K number of bright-blood images and the corresponding one of the K number of enhanced black-blood images to obtain a first bright-blood image and a first black-blood image, comprises:
    for each of the K number of bright-blood images, taking the corresponding enhanced black-blood images as a reference, performing a coordinate transformation and an image interpolation to the bright-blood image by using a similarity measure based on the mutual information and adopting a predetermined search strategy to thereby obtain a pre-registered first bright-blood image; and
    extracting content of an area same as a scanning range of the first bright-blood image from the corresponding enhanced black-blood image to form the first black-blood image.

4. The recognition method according to claim 3, wherein the registering the images in each layer of the bright-blood Laplacian pyramid with the image in a corresponding layer of the black-blood Laplacian pyramid to obtain a registered bright-blood Laplacian pyramid, comprises:

for each layer of the bright-blood Laplacian pyramid and the black-blood Laplacian pyramid, taking the black-blood Laplacian image corresponding to the layer as a reference image and the bright-blood Laplacian image corresponding to the layer a floating image, realizing an image registration by using the similarity measure based on the mutual information and the predetermined search strategy to thereby obtain a registered bright-blood Laplace image of the layer; and forming the registered bright-blood Laplacian pyramid from bottom to top according to a multi-layer bright-blood Laplacian image according to an order of decreasing resolution;

wherein the black-blood Laplacian image is an image in the black-blood Laplacian pyramid, and the bright-blood Laplacian image is an image in the bright-blood Laplacian pyramid.

5. The recognition method according to claim 4, wherein the registering the images in respective layers of the bright-blood Gaussian pyramid with the images in corresponding layers of the black-blood Gaussian pyramid respectively from top to bottom by using the registered bright-blood Laplace pyramid as superposition information to obtain a registered bright-blood Gaussian pyramid, comprises:

for a j-th layer from top to bottom of each of the bright-blood Gaussian pyramid and the black-blood Gaussian pyramid, using a black-blood Gaussian image corresponding to the j-th layer of the black-blood Gaussian pyramid as a reference image, a bright-blood Gaussian image corresponding to the j-th layer of the bright-blood Gaussian pyramid as a floating image, using the similarity measure based on the mutual information and the predetermined search strategy to obtain a registered bright-blood Gaussian image of the j-th layer;

performing an up-sampling operation on the registered bright-blood Gaussian image of the j-th layer, adding the registered bright-blood Gaussian image of the j-th layer after the up-sampling operation with a registered bright-blood Laplacian image of a corresponding layer of the registered bright-blood Laplacian pyramid to obtain an added image, and replacing a bright-blood Gaussian image of a (j+1)th layer of the bright-blood Gaussian pyramid by the added image; and taking a black-blood Gaussian image of the (j+1)th layer of the black-blood Gaussian pyramid as a reference image and the bright-blood Gaussian image of the (j+1)th layer after the replacing as a floating image, using a predetermined similarity measure and a predetermined search strategy to realize the registering and thereby obtain a registered bright-blood Gaussian image of the (j+1)th layer;

wherein j=1, 2, . . . , m−1; each the black-blood Gaussian image is one of the m number of images of the black-blood Gaussian pyramid, and each the bright-blood Gaussian image is one of the m number of images of the bright-blood Gaussian pyramid.

6. The recognition method according to claim 1, wherein the performing an elimination operation of flowing void artifact to the K number of enhanced black-blood images of the enhanced black-blood image group by using the registered bright-blood image group, to obtain an artifact-elimination enhanced black-blood image group comprising K number of object enhanced black-blood images, comprises:

improving contrast of each of the K number of registered bright-blood images to obtain a contrast-enhanced bright-blood image, thereby obtaining K number of contrast-enhanced bright-blood images;

extracting blood information from each of the K number of contrast-enhanced bright-blood images to obtain K number of bright-blood feature images;

fusing each of the K number of bright-blood feature images with the enhanced black-blood image corresponding to the registered bright-blood image according to a preset image fusion formula to obtain the object enhanced black-blood image of elimination of flowing void artifact corresponding to the enhanced black-blood image; and obtaining the artifact-elimination enhanced black-blood image group according to the object enhanced black-blood images respectively corresponding to the K number of enhanced black-blood images.

7. The recognition method according to claim 6, wherein the extracting blood information from each of the K number of contrast-enhanced bright-blood images to obtain K number of bright-blood feature images, comprises:

determining a first threshold by using a preset image binarization method;

extracting the blood information from each of the K number of contrast-enhanced bright-blood images by using the first threshold; and obtaining the bright-blood feature image according to the extracted blood information.

8. The recognition method according to claim 1, wherein the establishing a blood 3D model by using the registered bright-blood image group, based on transfer learning, comprises:

projecting the registered bright-blood image group in three preset directions by using a maximum intensity projection (MIP) method to obtain MIP images in the three preset directions;

taking the MIP images as a target domain and fundus vascular images as a source domain, and obtaining two-dimensional (2D) vascular segmentation images respectively corresponding to the MIP images in the three preset direction based on the transfer learning;

synthesizing the 2D vascular segmentation images in the three preset directions by using a back projection method to obtain a first 3D vascular volume data, wherein voxel values of a vascular part in the first 3D vascular volume data each are 0, and voxel values of a non-vascular part each are negative infinity; and obtaining the blood 3D model based on the first 3D vascular volume data and a second 3D vascular volume data corresponding to the registered bright-blood image group.

9. The recognition method according to claim 8, wherein the taking the MIP images as a target domain and fundus vascular images as a source domain, and obtaining 2D vascular segmentation images respectively corresponding to the MIP images in the three preset direction based on the transfer learning, comprises:

obtaining a pre-trained target neural network for a segmentation task of the fundus vascular images, wherein the pre-trained target neural network is obtained by pre-training according to a dataset of the fundus vascular images and an U-net network model;

performing gray inversion and contrast enhancement to the MIP images in the three preset directions to thereby obtain feature MIP images corresponding to the MIP images, wherein the feature MIP images have a same sample distribution as the fundus vascular images; and inputting the feature MIP images in the three preset directions into the target neural network to obtain the 2D vascular segmentation images corresponding to the feature MIP images.

10. The recognition method according to claim 1, wherein the obtaining values of target parameters representing degrees of vascular stenosis of respective vascular segments of the intracranial vascular enhanced 3D model, and marking the intracranial vascular enhanced 3D model by using the values of the target parameters of the respective vascular segments, to obtain an intracranial vascular lesion recognition model, comprises:

segmenting each of the vascular segments of the intracranial vascular enhanced 3D model from preset three directions to obtain 2D cross-sectional images respectively corresponding to the three preset directions;

performing corrosion operations on the vascular segments of the 2D cross-sectional images corresponding to the three preset directions, and recording a target corrosion times when the vascular segments are corroded until a single pixel;

obtaining the value of the target parameter representing the degree of vascular stenosis of each of the vascular segments according to the target corrosion times of the vascular segment respectively corresponding to the three preset directions; and marking the intracranial vascular enhanced 3D model by using the value of the target parameter of each of the vascular segments to obtain the intracranial vascular lesion recognition model.

* * * * *